United States Patent [19]
Thierry

[11] Patent Number: 6,110,490
[45] Date of Patent: *Aug. 29, 2000

[54] LIPOSOMAL DELIVERY SYSTEM FOR BIOLOGICALLY ACTIVE AGENTS

[75] Inventor: Alain R. Thierry, Strasbourg, France

[73] Assignee: The United States of America as represented by the Department of Health and Human Services, Washington, D.C.

[*] Notice: This patent is subject to a terminal disclaimer.

[21] Appl. No.: 08/522,246

[22] PCT Filed: Aug. 4, 1995

[86] PCT No.: PCT/US95/09867

§ 371 Date: Jan. 29, 1996

§ 102(e) Date: Jan. 29, 1996

Related U.S. Application Data

[63] Continuation-in-part of application No. 08/286,730, Aug. 5, 1994.

[51] Int. Cl.$^7$ ..................................................... A61K 9/127
[52] U.S. Cl. ............................. 424/450; 424/400; 935/54
[58] Field of Search ................................ 424/450; 935/54

[56] References Cited

U.S. PATENT DOCUMENTS

| | | | |
|---|---|---|---|
| 5,171,678 | 12/1992 | Behr | 435/172.3 |
| 5,279,833 | 1/1994 | Rose | 424/450 |
| 5,283,185 | 2/1994 | Epand | 435/172.3 |

FOREIGN PATENT DOCUMENTS

| | | |
|---|---|---|
| 93/05162 | 3/1993 | WIPO . |
| 94/05624 | 3/1994 | WIPO . |

OTHER PUBLICATIONS

F. Barthel et al., "Laboratory Methods—Gene Transfer Optimization with Lipospermine–coated DNA," DNA and Cell Biology, vol. 12, No. 6, 1993, pp. 553–560.

N. Zhu et al., "Systematic Gene Expression After Intravenous DNA Delivery into Adult Mice," Science, vol. 261, Jul. 9, 1993, pp. 209–211.

K. Yoshimura et al., "Adenovirus–Medicated Augmentation of Cell Transfection with Unmodified Plasmid Vectors," The Journal of Biological Chemical, No. 4 Issue, Feb. 3, 1993, pp. 2300–2303.

H. Farhood et al., "Effect of Cationic Cholesterol Derivatives on Gene Transfer and Protein Kinase C Activity," Biochimica et Biphysica Acta, (1992) pp. 239–246.

R. J. Cristiano et al., "Hepatic Gene Therapy: Adenovirus Enhancement of Receptor–Mediated Gene Delivery and Expression in Primary Hepatocytes," Genetics, vol. 90, Mar. 1993, pp. 2122–2126.

X. Gao et al., "A Novel Cationic Liposome Reagent for Efficient Transfection of Mammalian Cells," Biochemical and Biophysical Research Communications, vol. 179, No. 1, Aug. 30, 1991, pp. 280–285.

E. G. Nabel et al., "Site–Specific Gene Expressing In Vivo By Direct Gene Transfer Into the Arterial Wall," Science, vol. 249, Sep. 14, 1990, pp. 1285–1288.

J. P. Behr et al., "Efficient Gene Transfer Into Mammalian Primary Endocrine Cells with Lipopolyamine–Coated DNA," Proc. Nat'l Acad. Sci. vol. 86, Sep. 1989, pp. 6982–6986.

(List continued on next page.)

Primary Examiner—Thurman K. Page
Attorney, Agent, or Firm—Morgan & Finnegan, L.L.P.

[57] ABSTRACT

The present invention is directed to a liposomal preparation which is based on specific lipid components. The liposomal compounds are also combined with a biologically active agent, forming liposomal compounds. These compounds are useful in drug delivery, where specific therapeutic compounds are provided in the liposomes. The specific lipid components of the present invention provide a highly efficient and stable delivery system for nucleic acids. Consequently, one embodiment of the invention provide the liposomal preparations which are suitable for use in gene therapy.

21 Claims, 22 Drawing Sheets

OTHER PUBLICATIONS

P.L. Felgner et al., "Lipofection: A Highly Efficient, Lipid–Mediated DNA–Transfection Procedure," Proc. Nat'l Acad. ci., vol. 84, Nov. 1987, pp. 7413–7417.

C. Yen Wang et al., "pH–Sensitive Immunoliposomes Mediate Target–Cell Specific Delivery and Controlled Expression of A Foreign Gene in Mouse," Proc. Nat'l Acad. Sci., vol. 84, Nov. 1987, pp. 7851–7855.

P. Soriano et al., "Targeted and Nontargeted Liposomes for In Vivo Transfer to Rat Liver Cells of A Plasmid Containing The Plasmid I Gene," Proc. Nat'l Acad. Sci., vol. 80, Dec. 1983, pp. 7128–7131.

Gao Xiang et al., "Cationic Liposomes and Polymers for Gene Transfer", Journal of Liposome Research, vol. 3, No. 1, 1993, pp. 17–30.

B. Clary et al., "Adeno–Associated Virus Plasmid: Cationic Liposomal–Mediated Gene Transfer Results in Significant Cytokine Gene Expression in Human Tumor Cells Following Lethal Irradiation," Surgical Forum, vol. 44, 1994, pp. 530–533.

Farhood BBA 1111 p. 239 (1992).

Zhu, Science 261, Jul. 1993 p. 209.

Felgner PNAS 84, p. 7413 Nov. 1987.

Bhr. PNAS 86, p. 6982 Sep. 1989.

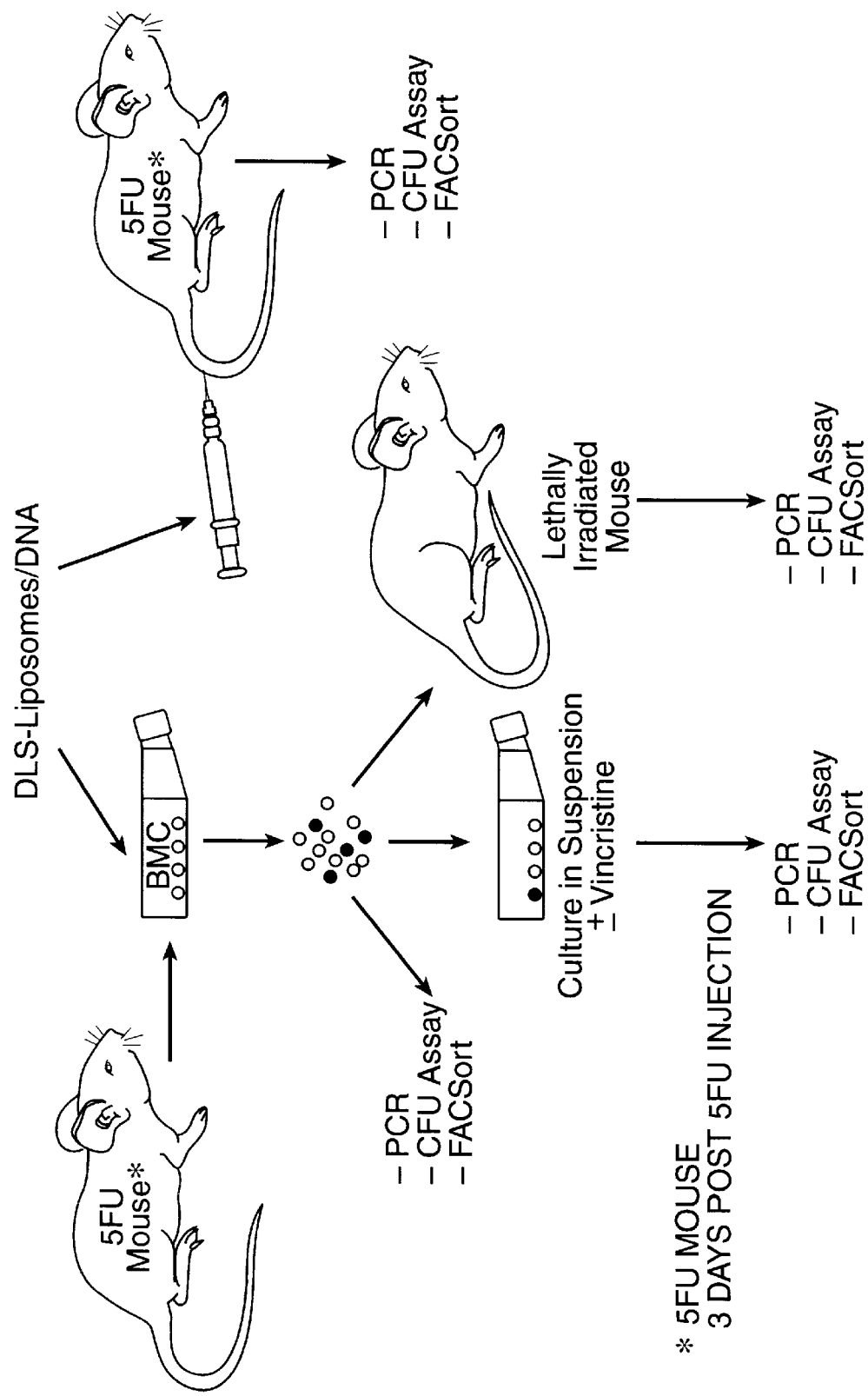

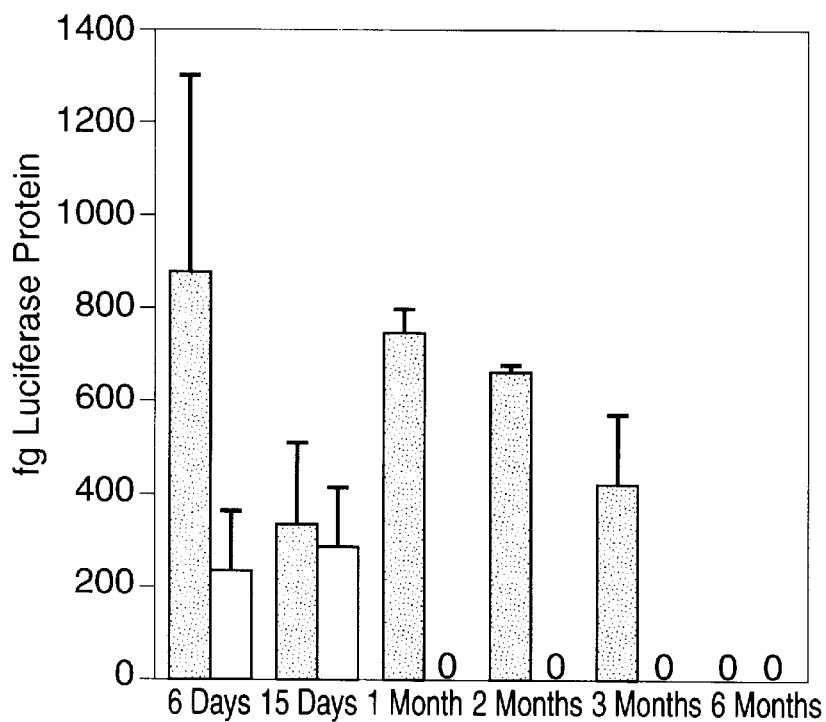
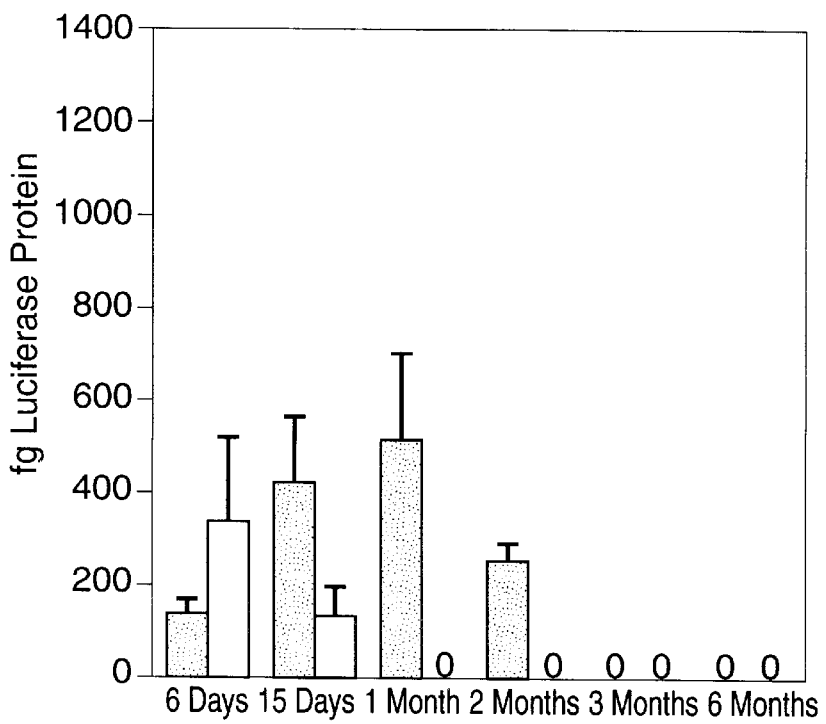

LIPOSOMAL DELIVERY SYSTEM FOR BIOLOGICALLY ACTIVE AGENTS

This application is a 371 of PCT/US95/09867 filed Aug. 4, 1995 and a C-I-P of Ser. No. 08/286,730, filed Aug. 5, 1994.

FIELD OF THE INVENTION

The present invention is directed to a liposomal preparation which is based on a composition of specific lipids which form liposomes. It is also an object of the present invention to provide a method for preparing a liposomal composition carrying a biologically active agent which is simple and very efficient. The liposomal delivery system of the present invention is used as a highly efficient transfer therapy method.

BACKGROUND OF THE INVENTION

Lipidic particles have been shown to be efficient vehicles for many in vitro and in vivo applications. Lipidic particles complexed with DNA have been used in vitro (Felgner P. L., et al. *Proc. Natl. Acad. Sci. USA* 84, 7413–7417 (1987); Gao X. et al. *Biochem. Biophys. Res. Commun.* 179, 280–285 (1991)) and in vivo (Nabel E. G., et al. *Science* 249, 1285–1288 (1990); Wang C. et al. *Proc. Natl. Acad. Sci. USA* 84, 7851–7855 (1987); Zhu N., et al. *Science* 261, 209–211 (1993); Soriano P., et al. *Proc. Natl. Acad. Sci. USA* 80, 7128–7131 (1983)) for the expression of a given gene through the use of plasmid vectors. Formation of complexes of DNA with cationic lipidic particles has recently been the focus of research of many laboratories. In particular, lipofectin™ (Gibco BRL, Gaithersburg, Md.) has been successfully used for the transfection of various cell lines in vitro (Felgner P. L., et al. *Proc. Natl. Acad. Sci. USA* 84, 7413–7417 (1987)) and for systemic gene expression after intravenous delivery into adult mice (Zhu N., et al. *Science* 261, 209–211 (1993)).

Lipidic particles may be complexed with virtually any biological material. These particles may be complexed with proteins, therapeutic agents, chemotherapeutic agents, and nucleic acids and provide a useful delivery system for these agents. One such drug delivery system, gene therapy, is one such area which has produced promising results. In this area two different strategies have emerged: Gene therapy and oligonucleotide-based therapeutics. To be successful these two approaches must be mediated by an efficient "in vivo" transfer of the nucleic acid material to the target cells and there is a need to provide an efficient and safe delivery system of nucleic materials.

Gene therapy may involve the transfer of normal, functional genetic material into cells to correct an abnormality due to a defective or deficient gene product. Typically, the genetic material to be transferred should at least contain the gene to be transferred together with a promoter to control the expression of the new gene.

Viral agents have been demonstrated to be highly efficient vectors for the transfection of somatic cells. Retroviruses in particular have received a great deal of attention because they not only enter cells efficiently, but also provide a mechanism for stable integration into the host genome through the provirus. However, clinical use of retroviral vectors is hampered by safety issues. A first concern is the possibility of generating an infectious wild type virus following a recombination event. A second concern is the consequences of the random integration of the viral sequence into the genome of the target cell which may lead to tumorigenic event. In addition, as retroviruses would only complete their life cycle in dividing cells, a retroviral vector would be inefficient in targeting cells which are not dividing. DNA viruses such as adenoviruses are potential gene carriers but this strategy is limited in the size of the foreign DNA adenoviruses can carry and because of the restricted host range. However, the advantage of adenoviruses over retroviral vectors is their ability to infect post-mitotic cells.

Synthetic gene-transfer vectors have been subject to intense investigation since this strategy appears to be clinically safe. Potential methods of gene delivery that could be employed include DNA/protein complexes (Cristiano R. J., et al. *Proc. Natl. Acad. Sci. USA* 90, 2122–2126 (1993)) or lipidic particles (Nabel E. G., et al. *Science* 249, 1285–1288 (1990); Felgner P. L., et al. *Proc. Natl. Acad. Sci. USA* 84, 7413–7417 (1987); Wang C. et al. *Proc. Nat. Acad. Sci. USA* 84, 7851–7855 (1987); Gao X. et al. *Biochem. Biophys. Res. Commun.* 179, 280–285 (1991); Zhu N., et al. *Science* 261, 209–211 (1993); Soriano P., et al. *Proc. Natl. Acad. Sci. USA* 80, 7128–7131 (1983)). The genetic material to be delivered to target cells by these methods are plasmids. Plasmids are autonomous self-replicating extra chromosomal circular DNA. They can be modified to contain a promoter and the gene coding for the protein of interest. Such plasmids can be expressed in the nucleus of transfected cells in a transient manner. In rare events, the plasmids may be integrated or partly integrated in the cell host genome and might therefore be stably expressed. Episomal plasmid vectors are plasmids able to replicate in the nucleus of the transfected cells and may therefore be expressed in a total growing cell population. Plasmids have a promising potential considering the fact that they may be applied in combination with a synthetic vector as carrier and that gene therapy by this means may be safe, durable, and used as drug-like therapy.

Plasmid preparation is simple, quick, safe, and inexpensive representing important advantages over retroviral vector strategy. The successful use of this genetic tool for "in vivo" approaches to gene therapy will rely on the development of an efficient cell delivery system.

Retroviral vectors have been shown to be very efficient for gene therapy. However, their use for in vitro human gene therapy has several limitations. Retroviral vectors may, by insertional mutagenesis lead to activation of oncogenes and increase the frequency of malignant transformation. They will not transfect non dividing cells, and their stability and titer are adversely affected by large gene insert. Adenoviral vectors which give rise to transient expression are currently limited by a demonstrated toxicity in vivo. Presently, replication-compromised herpes simplex virus vectors have toxic effects on the cells they infect, thus limiting their use for human trials. These obstacles have led several laboratories to develop physical means of gene transfer such as the pneumatic DNA gun (Yang et al. 1990 *Proc. Natl. Acad. Sci. USA* 9568–72), direct DNA injection (Wolff et al. 1990 *Science* 247:1465–68), or liposome delivery vector (Fergner et al. *Proc. Natl. Acad. Sci. USA* 1987 84:7413–17).

The fact that viral vectors have limitations such as propensity for recombination, low titer, and induction of host immunity has initiated research into non-viral vectors. The delivery of plasmid DNA via synthetic carriers to cells "in vivo" by direct i.v. administration is appealing because of its simplicity and potential to reach a far greater number of cells than by an "ex vivo" approach. Although the efficiency of "in vivo" transfection of DNA plasmids is limited when compared to delivery by viral vectors, recent advances, especially in lipidic particle delivery, have demonstrated that non-viral gene transfer offers exciting potential, including its use in a clinical setting. More recent attempts to deliver gene or antisense oligonucleotides has provided a new impetus to lipid particle technology (Leonetti, J. P., et al. (1990) *Proc. Natl. Acad. Sci. USA* 87, 2448–2451; Burch, R. M. et al. (1991) *J. Clin. Invest.* 88, 1190–1196; Thierry, A. R. et al. (1992) *Nucleic Acids Res.* 20, 5691–5698; Smith, J. G., et al. (1993) *Biochim. Biophys. Acta* 1154, 327–340). One such approach is based on the formation of complexes of DNA with cationic lipidic particles. A few therapeutic clinical trial protocols using local administration of these complexes are ongoing but data on systemic administration is still poorly documented (Wang C. et al. (1987) *Proc. Natl. Acad. Sci. USA* 84, 7851–7855; Zhu, N. et al. (1993) *Science* 261, 209–211).

Several lipids have been used in attempts to prepare liposome-like particles. One such lipid mixture is Lipofectin™ which is formed with the cationic lipid DOTMA, N[1-(2,3-dioleyloxy)propyl]-N,N,N-trimethyl-ammonium chloride, and DOPE, dioleylphosphatidyl ethanolamine at a 1:1 molar ratio. The lipidic particles prepared with this formulation spontaneously interact with DNA through the electrostatic interaction of the negative charges of the nucleic acids and the positive charges at the surface of the cationic lipidic particles. This DNA/liposome-like complex fuses with tissue culture cells and facilitates the delivery of functional DNA into the cells (Felgner P. L., et al. *Proc. Natl. Acad. Sci. USA* 84, 7413–7417 (1987)). New cationic lipid particles have been developed: Lipofectamine™ (Gibco BRL), composed of DOSPA, 2,3-dioleyloxy-N[2 (sperminecarboxamido)ethyl]-N,N-dimethyl-1-propanaminium trifluoracetate and DOPE at a 1:1 molar ratio. Lipofectace™ (Gibco BRL) composed of DDAB, dimethyidioctadecylammonium chloride and DOPE at a 1:1 molar ratio. DOTAP™ (Boehringer Mannheim, Ind.) is 1-2-dioleoyloxy-3 (trimethyl ammonia) propane.

Behr et al. (*Proc. Natl. Acad. Sci. USA* 86, 6982–6986 (1989); Barthel F., et al. *DNA Cell Biol.* 12, 6, 553–560 (1993)) have recently reported the use of a lipopolyamine (DOGS, Spermine-5-carboxy-glycinediotade-cylamide) to transfer DNA to cultured cells. Lipopolyamines are synthesized from a natural polyamine spermine chemically linked to a lipid. For example, DOGS is made from spermine and dioctadecylamidoglycine (Behr J. P., et al. *Proc. Natl. Acad. Sci. USA* 86, 6982–6986 (1989)). DOGS spontaneously condense DNA on a cationic lipid layer and result in the formation of nucleolipidic particles. This lipospermine-coated DNA shows high transfection efficiency (Barthel F., et al. *DNA Cell Biol.* 12, 6, 553–560 (1993)).

However, the above-described lipid compositions fail to produce liposomes. Rather, these investigations synthesized lipid particles, which are clusters of lipid molecules which have not formed at least a lipid bilayer membrane and therefore also lack an aqueous internal space. Since these particles are mere clusters of lipid molecules, the particles lack the ability to act as storage units for biologically active agents contained therein.

Therefore it is an object of the present invention to provide a liposomal composition capable of carrying internally biologically active agents.

It is an other object of the present invention to provide an efficient, stable and safe liposome-based delivery system for biologically active materials.

Yet another object of the present invention to provide a novel liposomal composition comprising a cationic lipopolyamine and a neutral lipid.

It is yet another object of the present invention to provide a method of transferring biologically active agents into cells and patients using the instant liposomal delivery system.

It is a further object of the present invention to provide a method of preparing liposomes, useful in providing efficient transfer therapy.

Yet a further object of the present invention relates to providing a method for long-term expression of a gene product from a non-integrated transgene in a patient.

SUMMARY OF THE INVENTION

The present invention relates to liposome compositions and a method of preparing such liposomes. In addition, the present invention relates to the administration of the biologically active agent-liposome preparations to cells and further to the administration of the liposome preparations to patients as a therapeutic agent.

The liposome compositions of the present invention provide highly efficient delivery of biologically active agents to cells. Liposome vesicles are prepared from a mixture of a cationic lipopolyamine and a neutral lipid and form a bi- or multilamellar membrane structure (referred to herein as "DLS-liposomes") A preferred embodiment of the present invention uses a spermine-5-carboxy-glycinedioctadecylamide (referred to herein as "DOGS") as the cationic lipopolyamine and dioleylphosphatidyl ethanolamine (referred to herein as "DOPE") as the neutral lipid.

The liposomes of the present invention efficaciously deliver biologically active agents into the cytoplasmic compartment of human cells. Use of such liposomal vehicles make possible high transfection efficiency of biologically active materials into cells.

The present invention also encompasses a method of preparing such a liposome composition. The presence of at least one neutral lipid in combination with at least one cationic lipopolyamine makes possible the formation of liposomes after hydration. According to the method of the present invention, liposomes are prepared by mixing together each of a cationic lipopolyamine and a neutral lipid in a molar ratio ranging from a ratio of 0.02:1 to a ratio of 2:1; evaporating the mixture to dryness; and rehydrating. In order to introduce a biologically active agent into the liposomes, such agent can be added prior to or after rehydration of the dried film.

In one aspect of the invention, nucleic acids may be associated with the liposomes. This association may be accomplished in at least in two ways: (1) complex formation between the cationic liposome vesicle and negatively charged polyaminon, such as nucleic acid or (2) encapsulation in the cationic liposome vesicle.

The present invention is further directed to a method of treating a subject with a suitable pharmaceutical formulation of nucleic acid-liposomes in order to deliver specific nucleic acids to target cells of the subject. Such a method of treating subjects provides effective delivery of oligonucleotides or gene-expressing nucleic acid vectors (e.g. plasmids or viral vectors) into cells. Therefore, such a method of drug delivery is useful for the transport of nucleic acid based therapeutics.

Another embodiment of the present invention is directed to a combination of a DOGS/DOPE liposome preparation externally anchored through hydrophobic interactions with an adenovirus particle. Since adenoviruses enter cells via receptor-mediated endocytosis, the combination of adenovirus particles and the DLS-liposomes produces an enhanced transduction efficiency.

Adenovirus particles may also serve as a nucleic acid which is carried in the liposome internally.

The present invention provides a therapeutic method of treating ailments and conditions based upon a liposome-facilitated transfer of biologically active agents. For example, the present invention provides a pharmaceutical liposomal formulation for the delivery of nucleic acids using systemic administration to provide long-term expression of a given gene. One such method provides direct systematic nucleic acid transfer combining the DLS-liposomes with episomally replicative DNA vectors carrying the nucleic acid of interest. Alternatively in vitro cell transfection followed by tissue transplantation such that the transfected cells are incorporated in transplanted tissue. This method is referred to as in vitro/ex vivo transfer. Other biologically active agents may be encapsulated in the liposomes of the present invention and delivered to cells using systemic or in vitro/ex vivo transfer methods.

BRIEF DESCRIPTION OF THE DRAWINGS

FIG. 7: Protocol for liposomal transfection of mouse BMC.

FIGS. 18A–18D: Time course of luciferase expression in different tissues. 75 μg of pBKd2CMV-luc (closed bars) or pCMVintlux (open bars) plasmid DNA were administered i.v. and luciferase activity was assayed in lung, spleen, liver and heart up to 6 months post-injection. Values are the means (±S.D.) of triplicate determination from three different mice.

DETAILED DESCRIPTION OF THE INVENTION

Figure 1:
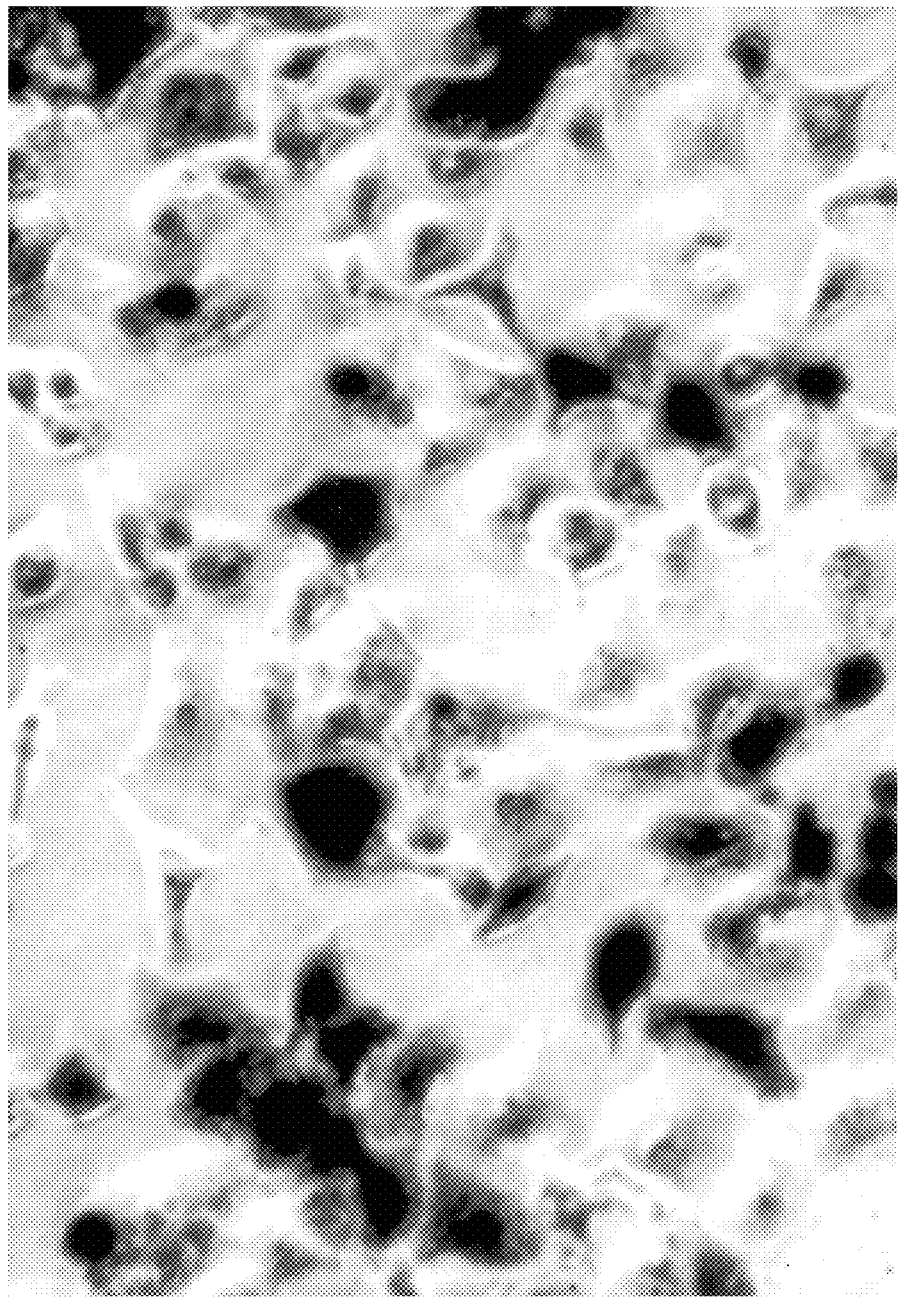
FIG. 1: β-Galactosidase expression in HeLa cells transfected with DOGS/DOPE liposomes.

The present invention relates to the discovery that biologically active agents may be associated with liposomes of a specific composition forming a stable structure. The liposome containing a biologically active agent may then be injected into a mammalian host to effectively deliver its contents to a target cell. One such example comprises encapsulating a nucleic acid within a liposome and expressing a gene encoded on the nucleic acid within the target host cell, through the use of plasmid DNA. Conversely the expression of a gene may be inhibited through the use of antisense oligonucleotides. Alternatively a chemotherapeutic agent may act as the biologically active agent and be encapsulated within a liposome. The efficiency of a liposome-mediated drug delivery system is directly dependent upon the liposome composition and its resulting association with cellular membranes.

"Biologically active agents" as the term is used herein refers to molecules which effect a biological system. These include molecules such as proteins, nucleic acids, therapeutic agents, vitamins and their derivatives, viral fractions, lipopolysaccharides, bacterial fractions and hormones.

The term "protein" includes any proteaceous material such as peptides, protein fragments, protein conjugates, glycoproteins, proteoglycans, cytokines, hormones and growth factors.

The term "therapeutic agents" refers to any drug whose delivery could be affected with liposomes. Therapeutic agents of particular interest are chemotherapeutic agents, which are used in the treatment and management of cancer patients. Such molecules are generally characterized as antiproliferative agents, cytotoxic agents and immunosuppressive agents and include molecules such as taxol, toxorubicin, daunorubicin, vinca-alcaloide, actinomycin and toposites.

The term "nucleic acids" means any double strand or single strand deoxyribonucleic acid (DNA) or ribonucleic acid (RNA) of variable length. Nucleic acids include sense and anti-sense strands. Nucleic acid analogs such as phosphorothioates, phosphoramidates, phosphonates analogs are also considered nucleic acids as that terms is used herein. Nucleic acids also include chromosomes and chromosomal fragments.

Antisense oligonucleotides may potentially be designed to specifically target genes and consequently inhibit their expression. In addition this delivery system may be a suitable carrier for other gene-targeting oligonucleotides such as ribozymes, triple helix forming oligonucleotides or oligonucleotides exhibiting non-sequence specific binding to a particular proteins of other intracellular molecules. For example, the genes of interest may include retroviral or viral genes, drug resistance genes, oncogenes, genes involved in the inflammatory response, cellular adhesion genes, hormone genes, abnormally overexpressed genes involved in gene regulation.

Such nucleic acids may be associated with a liposome composition in accordance with this invention. In one embodiment of the present invention, modified or unmodified phosphodiester oligonucleotides (alternatively referred to as "oligo(dN)") are used as nucleic acids. These analogs provide increased nuclease protection and increased cellular transport.

"Liposome" as the term is used herein refers to a closed structure comprising of an outer lipid bi- or multi-layer membrane surrounding an internal aqueous space. Liposomes can be used to package any biologically active agent for delivery to cells. For example, DNA can be packaged into liposomes even in the case of plasmids or viral vectors of large size which could potentially be maintained in a soluble form. Such liposome encapsulated DNA is ideally suited for direct application to in vivo systems by a simple intravenous injection. These liposomes may entrap compounds varying in polarity and solubility in water and other solvents. The liposomes are generally from a bilayer membrane in a uni- or multilamellar membranous structure. Generally these liposomes may form hexagonal structures, and suspension of multilamellar vesicles.

The lipid mixture of the present invention comprises a cationic lipopolyamine compound. Cationic lipopolyamines useful in the present invention include cationic lipid derivatives of polyamines, spermidine and spermine as well as others well-known in the art (Theoharides, 1980 Life Sci. 27:703–713; Stevens, 1981 Med. Biol. 59:308–313; Morris, Marton Eds., Polyamines in Biology & Med., Dekker, N.Y., N.Y., p. 512; U.S. Pat. No. 5,171,678 and U.S. Pat. No. 5,283,185, all of which are incorporated herein by reference). Examples of cationic lipopolyamines include 2,3-dioleyloxy-N[2sperminecartoxamido)ethyl]-N,N-dimethyl-1-propanaminuim trifluoracetate, spermine-5-carboxy-glycinediotadecylamide and dipalmitoylphosphatidylethanolamidospermine. A preferred type of lipopolyamine comprises a lipid having a quaternary or tertiary amine group covalently attached.

These lipopolyamines can vary in chain length and may be present as mixtures of lipopolyamines in the liposome so long as the molar ratio of lipopolyamine to neutral lipid is maintained.

A preferred cationic lipopolyamine is DOGS.

In order to form stable liposomes, the cationic lipopolyamine is combined with a neutral lipid. Such neutral lipids include triglycerides, diglycerides and cholesterol and are known in the art, for example as described in U.S. Pat. No. 5,438,044 which is incorporated herein by reference. In particular a neutral phospholipid is preferred. More preferably, the neutral lipid is a neutral amino phospholipid. Most preferably, the neutral lipid comprises phosphatidylethanolamine (PE) or a derivative of PE such as DOPE (dioleoyl-phosphatidylethanolamine). Mixtures of neutral lipids may be used in the liposomes of the present invention so long as the molar ratio of lipopolyamine to neutral lipid is maintained.

Liposomes comprising at least one lipopolyamine and at least one neutral lipid, present in a molar ratio range of 0.02:1.0 to a ratio of 2.0:1.0 provide an effective drug delivery system. More preferably, the molar ratio of lipopolyamine to neutral lipid is 0.2:1 to a ratio of 0.9:1. For optimal transfection efficiency a cationic lipopolyamine/neutral lipid molar ratio of about 0.5:1 is used. The liposomal composition of the present invention has shown to be stable in a biological environment. In the case wherein a nucleic acids is the biologically active agent, it is demonstrated that nucleic acids associated with the liposomal carrier are completely protected from enzymatic attack, such as from nucleases, and that stability in circulating blood after administration may be achieved.

The liposome delivery system of the present invention comprises a specific mixture of lipids. These components are prepared such that a liposome is formed and the biologically active agent, such as a nucleic acid is contained therein.

Nucleic acids-based therapeutics are of broad use in therapy of a wide variety of diseases and disorders, such as, inherited or acquired genetic disease or viral infections. In addition, nucleic acid based therapeutics can be used to prevent drug resistance.

The present invention may utilize one or more nucleic acids or other biologically active molecules in conjunction with the liposomal carrier.

Method of Preparing DLS-Liposomes

In one embodiment of the present invention, the liposomes are prepared by drying a lipid mixture containing a cationic lipopolyamine and neutral lipid which are provided preferably in a molar ratio range of 0.02:1 to a ratio of 2.0:1. This dried film is then rehydrated. Several methods of associating biologically active agents, for example nucleic acids, with liposomes are described in this invention. The exemplified embodiment comprises hydrating a dried lipid film by introducing an aqueous solution, and completely dispersing it by strongly homogenizing the mixture with a vortex, magnetic stirrer and/or sonication. Subsequent liposomes are mixed with a nucleic acid solution allowing complex formation between positive charges of the lipopolyamine-containing liposomes and the negative charges of the nucleic acids. Such liposomes are referred to herein as DLS-liposome-1 or lipid complexes.

In another embodiment of the present invention the liposomes are formed by dissolving in chloroform at least one cationic lipopolyamine and at least one neutral lipid. After stirring by gentle vortexing, the mixture is evaporated to dryness. The subsequent dried lipid film is resuspended in a volume of water containing the biologically active agent. Formation of DLS-liposome is carried out by thorough stirring. Entrapment and/or assimilation of the biologically active agent by the DLS-liposomes is efficient and nearly complete.

The exemplified embodiment comprises hydrating the dried lipid film using a low and defined (5–10 $\lambda l/\mu g$ lipids) volume of aqueous solution containing concentrated nucleic acids. These liposomes are referred to herein as DLS-liposomes-2 or encapsulated lipsomes. Such concentrated nucleic acids are provided in a concentration greater than 1 mg/ml. A preferred concentration is about 2 mg/ml and the most concentrated form of nucleic acid will depend upon the concentration at which its viscosity is excessive, generally at a concentration of about 3 mg/ml. Dispersion is completed by strongly homogenizing the mixture using a vortex or magnetic stirrer. Nucleic acids are encapsulated in the liposomes during the formation and also are partly complexed through electrostatic interaction between the nucleic acid and the cationic liposomes.

In another embodiment of the present invention other biologically active agents are encapsulated in a DLS-liposome. The second method described above can be used with any biologically active material. Therefore, molecules such as chemotherapeutic agents can be introduced into the liposomes of the present invention by rehydrating the dried film in the presence of such agents.

The methods of forming liposomes of the present invention lead to liposome-complexed and liposome-encapsulated biologically active agents. Liposome-encapsulated biologically active agents have been shown to be more efficient in transducing cells in cell cultures. However, the ability to sonicate the lipid vesicles in the liposome-complexed biologically active agents allow for more homogenized and smaller liposome particles, and consequently for the ability to circulate for longer periods in blood following systemic injection.

Biologically active agents delivered using the delivery system of the present invention are efficiently released from endocytic vesicles, and as a result, a high cytoplasmic and nuclear distribution of biologically active agents is achieved.

Targeted Liposomes

The presence of a neutral lipid, such as DOPE, in combination with a cationic lipopolyamine such as DOGS makes possible the formation of liposomes upon rehydration, whereas use of a lipopolyamine alone only leads to the formation of lipid particles. Formation of phospholipidic bilayer or multilamellar membrane vesicles (liposomes) allows for a enhanced blood circulation, stability and effectiveness of cellular uptake. In addition, the liposomal membrane facilitates anchorage to its surface of other substituents, which can increase gene transfer and allow cell targeting, such as viral particles, virus fusogenic peptides specific ligands or antibodies.

Formation of liposomes make possible anchorage to the membrane layers of products which may increase transduction efficiency. Viruses, in general, are inherently excellent gene transfer vectors. Viral capsids or envelopes exhibit specific structure and contain molecules leading to efficient delivery of their genetic content to the infected cells. In order to exploit these properties, adenovirus particles (without DNA or denatured by irradiation) have been externally attached to the liposomal membrane of the liposomes prepared according to the present invention. It is established that adenoviruses enter cells via receptor-mediated endocytosis. A specific fusogenic mechanism makes possible the release of the viral genetic content from the cellular endocytic vesicles after internalization. Use of adenovirus to facilitate gene transfer has been reported (Cristiano R. J., et al. *Proc. Natl. Acad. Sci. USA* 90, 2122–2126 (1993)). Although DLS-liposomes clearly show a significant escape from intracellular vesicles, presence of adenovirus capsids at the liposome surface may enhance transduction efficiency by facilitating intracellular vesicle disruption.

Alternatively, tissue targeting may be obtained by anchoring antibodies or ligands at the surface of the liposomes. Cell specificity of such liposome mediated delivery may be of particular importance in targeting cancer cells and bone marrow stem cells.

The liposomal delivery system of the present invention may be used for increasing recombinant retrovirus and adenovirus infection. Retrovirus entry into cells is mediated via ligand-receptor recognition, and consequently their uptake is very low in certain cells which do not present those receptors. Associating a retrovirus or other recombinant virus such as adenovirus to be used for gene therapy onto the outside of the liposomes may enhance penetration and/or expression of the viral agents.

The liposomal delivery system of the present invention makes possible high transduction efficiency in any type of cell, including human adenocarcinoma, HeLa, murine carcinoma, NIH3T3, human embryonic kidney 293, human leukemia MOLT-3 cell lines, and primary cultures of human macrophages and human vascular endothelial cells.

Transfer Therapy Methods

The liposomal composition of the present invention may be systematically administered into patients parenterally in order to achieve transfer therapy of one or more biologically active agents. Moreover, this technique may be used for "ex vivo" transfer therapy where tissue or cells are removed from patients, then treated and finally reimplanted in the patient. Alternatively, systemic therapy is also effective in administering the DLS-liposome.

Many diseases can be treated via the drug delivery system of the present invention. Diseases such as diabetes, atherosclerosis, chemotherapy-induced multi-drug resistance, and generally, immunological, neurological and viral diseases can be treated using the present drug delivery system. One particular condition which can be treated via the system of the present invention relates to HIV and HIV-related diseases, such as anemia, leukopenia and thrombocytopenia. These clinical conditions are significantly related to a decrease or disappearance of hematopoietic progenitor cells in bone marrow of HIV-1 patients. Transfection of bone marrow stem cells, bone marrow stroma cells and embryonic stem with gene coding for immuno-restoring compounds might enhance the differentiation and proliferation capacity of such cells.

The delivery system of the present invention is also useful for correcting the ion transport defect in cystic fibrosis patients by inserting the human CFTR (cystic fibrosis transmembrane conductance regulator) gene. Oral administration such as nebulization could particularly suitable. In addition, DLS-liposomes can be used for the inhibition of tumor cells by administering in tumor cells a molecule inhibiting tumorigenesis or gene coding for an antisense oligonucleotides directed to mRNA transcripts of angiogenic factors. In addition, ribozymes may be encapsulated and enzymatically attach specific cellular contents. Intra-lesional or intravenous administration appear suitable for this case.

The ability to select bone marrow cells expressing a selectable gene which confers resistance to anti-cancer drugs would be useful to protect bone marrow during chemotherapy, but also could be helpful to select for cells co-transfected with genes needed in therapy of other diseases, including genetic defects manifested in bone marrow. One such selectable gene is the human MDR1 gene which confers cross-resistance to many cytotoxic drugs. The human MDR1 gene product is a 170 Kd glycoprotein (referred to herein as "P-gp") that works as an ATP dependent pump that effectively pumps out of cells many anti-cancer cytotoxic drugs, such as topside, teniposide, actinomycin D, doxorubicin, daunorubicin, taxol, or vinca alkaloids.

An exemplified embodiment of the present invention describes an efficient protocol for introducing the human MDR1 gene into hematopoietic cells both in vivo and in vivo using a liposomal delivery system. Transfection of hematopoietic cells followed by gene expression is demonstrated in at least three blood cell lineages.

Using the DLS-liposome system, the human MDR1 gene is introduced into bone marrow cells ("BMC"). The transferred human MDR1 is expressed, as detected by staining with P-gp specific MRK16 monoclonal antibody, in all of the in vitro transfected BMC. Moreover, P-gp is detected in BMC from all transplanted animals tested, and from almost all of the in vivo treated animals.

The expression of the MDR1 gene appears to be present for a period of at least 30–36 days, indicating that some of the transfected cells had been precursor cells, or long-lasting cells.

The potential for obtaining drug resistant bone marrow progenitor cells after gene transfer using the instant liposome delivery system make it possible to protect cancer patients undergoing chemotherapy from marrow toxicity of anti-cancer drugs. In addition, the multidrug resistance gene serves as a positive selectable gene marker in vivo for insuring the expression of a non-selectable gene.

Alternatively a systemic approach to transfer therapy may be utilized.

The DLS-liposomes containing the nucleic acid drug can be administered by intravenous, intramuscular, intraperitoneal, subcutaneous intra-lesional and oral means.

The development of the present liposome delivery system comprising DLS liposomes may be encapsulate episomal expression vectors so as to result in a broad biodistribution and persistence of transgene expression following a single intravenous ("i.v.") injection of liposomal DNA. The efficacy of DLS-liposomes used for the "in vivo" expression of the human MDR-1 gene is also disclosed in bone marrow progenitor cells by employing two different approaches: 1) a systemic delivery, and 2) an "ex vivo" approach by transplanting "in vitro" transfected BMC.

The long-term transgene expression observed using these delivery methods is due to the ability of DLS-liposomes to deliver significant amounts of DNA in to cells and tissues and to the use of human papovavirus ("BKV")-derived episomal expression vectors. Episomal vectors may be derived from the BKV contain a viral origin of DNA replication and a viral early gene that transactivates the viral DNA origin of replication, allowing for episomal replication in permissive cells. BKV-derived expression vector share the desirable qualities of extrachromosomal replication and thus a lack of a requirement of cellular division for the chromosomal replication of retroviral-based vectors. Moreover, extrachromosomal expression may lessen the possibility of attenuation of the transgene expression due to host cis-chromosomal effects. The BKV-derived episomes may persist in the progeny of transfected cells, whereas non-episomal vectors would not persist in a non-integrated form following cell division. Other episomal expression vectors include as Epstein-Barr virus derived vectors (Yates, J. L. et al. (1985) *Nature* 313, 812–815) and can also be used for "in vivo" gene transfer therapies.

Episomal expression constructs utilized in the present invention improve the persistence of transgene expression when compared with the use of non-episomal vectors. Using PCR analysis, detection of the transgene in various organs is possible and detection of the transgene mRNA persists for as long as 3 months. Transgene expression of the present invention declines slowly after a maximum level between 6 and 15 days post-injection and is detected for up to 3 months in various tissues. Original and episomally replicated forms of BKV-derived derived vectors are present in tissues 2 weeks post-injection suggesting episomal replication from this point on.

Episomal DNA vectors in combination with an efficient synthetic delivery system appears to be a particularly attractive approach for gene transfer therapy. The present invention designed BKV-derived episomal constructs which lack the expression of viral proteins (VP1, VP2 and VP3) so as to avoid the side effects associated with the expression of viral proteins. These constructs (pBKd2) retained high transfection efficiency and "in vivo" episomal replication.

A degree of tissue specific expression can be obtained depending upon the liposome preparation, the route of administration and the promoter driving expression of the transgene. Useful promoters are well-known to the skilled artisan and can be substantiated for those exemplified herein. It is clear that the more cationic (DNA/total lipid ratio <0.05, w/w) the liposomes, the more lung and heart are targeted. Although reporter gene expression may be lower following subcutaneous ("s.c.") administration of liposomal DNA compared to i.v. administration, there were no changes in tissue targeting. In contrast and as expected, after intraperitoneal ("i.p.") administration the spleen was particularly targeted. The present invention also demonstrates that the CMV promoter is capable of more efficient expression in spleen than in lung when compared to the RSV promoter. No significant difference has been observed in liver and heart. Thus, the choice of the promoter may greatly influence the efficacy of non-retroviral mediated gene delivery and may lead to a certain degree of tissue specificity.

In one embodiment of the present invention, the transgene expression following a single injection of liposomal DNA was investigated. It is clear that repeated injection may increase and/or prolong transgene expression. Then, desirable transgenes may be repetitively administered and thus offers an attractive alternatives to retroviral mediated gene therapy. Using the DLS-liposomes of the present invention administered via systemic delivery or aerosol delivery induced immunogenecity was observed when liposomal DNA was administrated at doses which produced detectable transgene expression.

A proposed daily dosage of active compound for the treatment of man is 0.5 mg DNA/kg to 4 mg DNA/kg, which may be conveniently administered in one or two doses. The precise dose employed will of course depend on the age and conditions of the patient and on the route of administration. Thus a suitable dose for administration by inhalation is 0.5 mg DNA/kg to 2 mg DNA/kg, for oral administration is 2 mg DNA/kg to 5 mg DNA/kg, for parenteral administration is 2 mg DNA/kg to 4 mg DNA/kg.

The compound of the invention may be formulated for parenteral administration by bolus injection or continuous infusion. Formulation for injection may be presented in unit dosage form in ampoules, or in multi-dose containers with an added preservative. The compositions may take such forms as suspension, solutions or emulsions in oily or aqueous vehicles, and may contain formulatory agents such as suspending, stabilizing and/or dispersing agents. Alternatively, the active ingredient may be in powder form for reconstitution with a suitable vehicle, e.g. sterile pyrogen-free water, before use.

The compounds according to the invention may be formulated for administration in any convenient way. The invention therefore includes within its scope pharmaceutical compositions comprising at least one liposomal compound formulated for use in human or veterinary medicine. Such compositions may be presented for use with physiologically acceptable carriers or excipients, optionally with supplementary medicinal agents. Conventional carriers can also be used with the present invention.

For oral administration, the pharmaceutical composition may take the form of, for example, tablets, capsules, powders, solutions, syrups or suspensions prepared by conventional means with acceptable excipients.

The following examples serve to illustrate further the present invention and are not to be construed as limiting its scope in any way.

All of the references mentioned in the present application are incorporated in toto into this application by reference thereto.

EXAMPLE 1

Preparation of a DOGS/DOPE liposome composition.

Liposomes are formed by mixing 1 mg DOGS and 1 mg DOPE (0.5:1 molar ratio). After thorough stirring, the mixture is evaporated to dryness in a round bottomed borosilicate tube using a rotary evaporator. The subsequent dried lipid film is resuspended in a low volume of ethanol (10 to 40 pl/mg lipid). Formation of liposomes is carried out by adding an excess of distillated water (at least 200 μl/mg lipid). After homogenization by slight vortexing, the mixture is incubated for at least 15 min. If needed, the resulting suspension may be sonicated in a fixed temperature bath at 25° C. for 15 min.

EXAMPLE 2

Preparation of a DOGS/DOPE liposome-nucleic acids complex composition.

Complex formation of nucleic acids to the liposome bilayer membrane is achieved by simply mixing the preformed DOGS/DOPE liposomes to a solution of nucleic acids. In an Eppendorf tube, DLS-liposomes are mixed in a 150 mM NaCl solution to nucleic acids at a concentration of 12.5 μg total lipids (liposomes)/μg nucleic acid for double strand DNA, and a concentration of 6 μg liposomes/1 μg nucleic acid for oligonucleotides. The mixture is slightly mixed and incubated for at least 30 min at room temperature. Complex formation is very effective and nearly complete since at least 80% of nucleic acids were assimilated into the liposomes. These liposomes are referred to as DLS-liposomes-1 or liposome complexes.

EXAMPLE 3

Alternatively, liposomes were formed by mixing 1 mg DOGS and 1 mg DOPE (0.5:1, molar ratio). After thorough stirring, the mixture is evaporated to dryness in a round bottomed borosilicate tube using a rotary evaporator. The subsequent dried lipid film is resuspended in a minimal volume (7 µl/mg lipid) of water solution containing nucleic acids (1400 µg/ml). Formation of liposomes is carried out by thorough stirring. The subsequent liposome preparation may be diluted in 150 mM NaCl. Entrapment and/or assimilation of nucleic acid by the liposomes is very efficient and nearly complete since at least 80% of nucleic acids are encapsulated by the liposomes. These liposomes are referred to as DLS-liposomes-2 or encapsulated liposomes.

EXAMPLE 4

In vitro Gene Transfection

Gene transfection efficacy was ascertained in vitro using reporter genes such as genes coding for β-galactosidase or luciferase. Two plasmid constructs containing the CMV (Clonetech) and RSV (Promega) promoters were used as genetic vectors for the β-galactosidase and luciferase genes, respectively. These plasmid vectors were delivered to the human carcinoma HeLa cells via the liposome carrier system in accordance with this invention. Either DLS-liposmes-1 or DLS-liposomes-2 are used in this example.

One microgram liposomal DNA (both DLS-liposmes-1 and 2) was added to the medium of a HeLa cell culture at a 50–700% confluency (500,000–700,000 cells/ml culture medium/7 $cm^2$ culture plate surface area). Cells were incubated at 37° C. with the liposomal DNA for at least 4 hr. Determination of gene expression was carried out for both types of plasmids following an incubation of 2–3 days at 37° C.

β-galactosidase activity was observed using a staining procedure after cell fixation on the culture plate using a conventional method. Cells expressing the β-galactosidase were readily identified by their intense blue staining. As shown in FIG. 1, more than 60% of the HeLa cells treated by DOGS/DOPE liposomal DNA, actively expressed β-galactosidase.

Luciferase activity was detected in HeLa cells using a standard method (Promega, Madison, Wis.). Luciferase gene containing plasmid was used for a comparative study of the transduction efficiency of the liposomal delivery in accordance with this invention and liposomal vectors commercially available. Optimal experimental conditions were used for each tested method.

Figure 2:
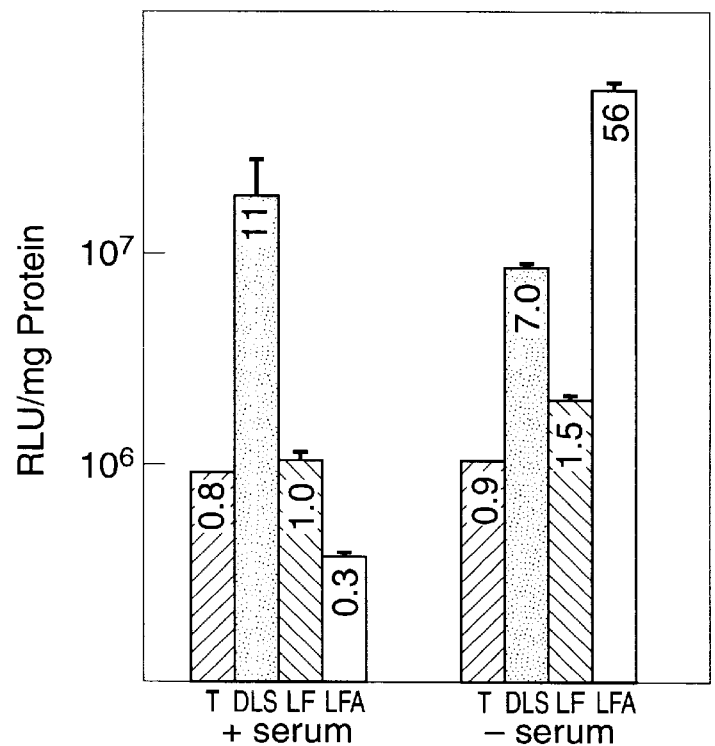
FIG. 2: Comparative study of the transfection efficiency of DLS and other liposomal delivery systems. Luciferase activity was assayed in HeLa cells transfected with pRSV-luc plasmid in presence or in absence of serum (15%) T: DOGS or Transfectam™ (Promega, Madison, Wis.); LF: Lipofectin™ (Gibco BRL, Gaithersburg, Md.); LFA: Lipofectamine™ (Gibco BRL).

In serum-containing cell culture medium, transduction efficiency in HeLa cells treated with the liposomal system in accordance with this invention appears to be 11-fold, 10-fold and 37-fold higher than that of DOGS or Transfecta™ (Promega, Madison, Wis.), Lipofectin™ and Lipofectamine™ (Gibco BRL, Gaithersburg), as shown in FIG. 2.

In serum-free medium, transduction efficiency using DLS-liposomes appears equivalent to that determined when cells are incubated in serum-containing medium. In contrast, use of Lipofectamine™ in serum-free conditions make possible a high transfection efficiency. The dramatic decrease in transduction efficiency (186-fold) using Lipofectamine™ in a medium containing fetal bovine serum (10%) emphasizes the high instability of DNA when exposed to nucleases, and the need for complete DNA protection from enzymatic attack in a biological environment. DOGS/DOPE liposomes prepared in accordance with the method described in example 2 and 3 exhibit an effective cell delivery and an efficient DNA protection during transport.

Figure 3:
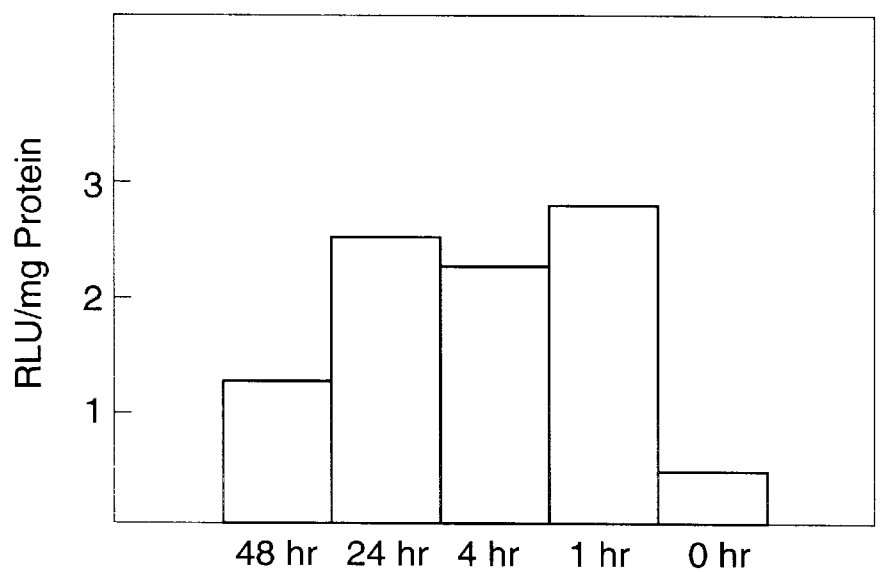
FIG. 3: Effect of preincubation in culture medium on DLS transfection efficiency in HeLa cells. Luciferase activity was ascertained following transfection of liposomal DNA pre-incubated in serum containing medium (15%).

As illustrated in FIG. 3, preincubation of liposomal DNA in serum containing medium up to 48 hours does not decrease transfection efficiency.

Figure 4:
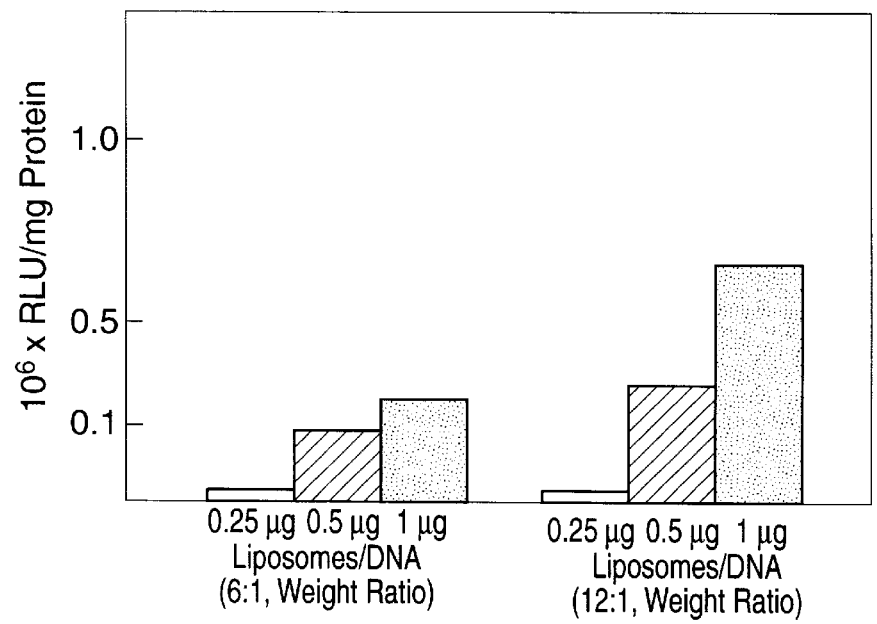
FIG. 4: Transfection efficiency in HeLa cells with liposomal DNA. Luciferase activity was determined.

FIG. 4 shows optimal transfection efficiency by using a 12:1 liposome/DNA weight ratio for the preparation of the liposomal DNA.

Figure 5:
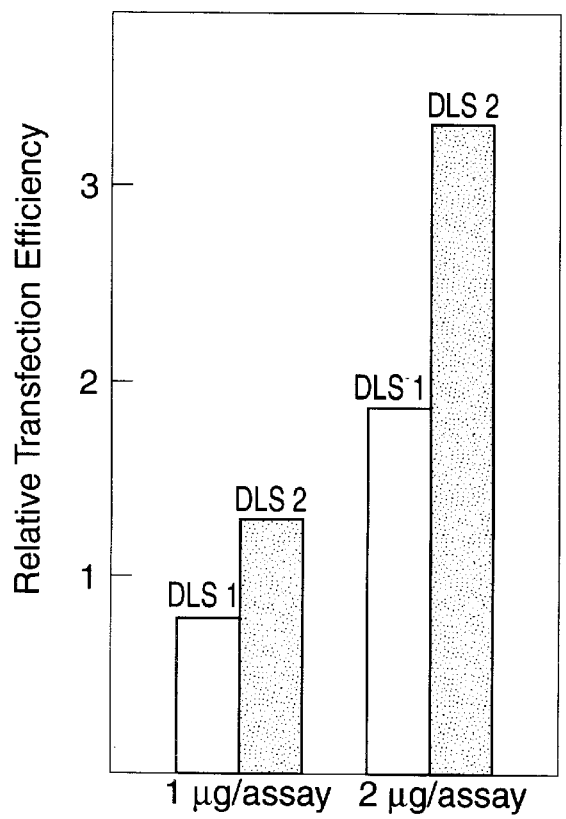
FIG. 5: Relative transfection efficiency of DLS-liposome-1 and DLS-liposome-2 in HeLa cells using pRSV-luc.

As illustrated in FIG. 5, use of plasmid DNA delivered by DLS-liposomes-2 showed better transduction efficiency in HeLa cells when compared to the DLS-liposomes-1 delivery. This may be due to increase in DNA protection from nuclease attack and/or better release from endocytic vesicles when encapsulated in liposomes.

EXAMPLE 5

Preparation of DOGS/DOPE Liposome Composition Containing Oligonucleotides

Oligonucleotides may be complexed or encapsulated in DLS-liposomes using the method described in example 2, respectively. The only modification is that a two-fold higher nucleic acid/liposome ratio is preferably used for DLS-liposomes-1 (20 µg/60 µg, weight ratio) to produce an equivalent complexing efficiency. This leads to a higher concentration of oligonucleotides complexed with the liposome preparation and consequently a higher efficiency of delivery in terms of quantity of nucleic acids delivered per cell.

EXAMPLE 6

Intracellular Distribution of Nucleic Acid After Delivery with DLS-Liposomes Nucleic acid cell penetration and its intracellular distribution following delivery using DLS-liposomes were observed using laser-assisted confocal microscopy and FITC-labeled oligodeoxyribonucleotides (20 mers). The former technique allows for the high resolution of optical sections of suspension cell preparations and can readily specify the intracellular distribution of a fluorescent compound. FIG. 6 presents images of hepatocyte HepG2 cells treated with DLS-1 encapsulated oligodeoxyribonucleotides for 24 hrs.

Figure 6A:
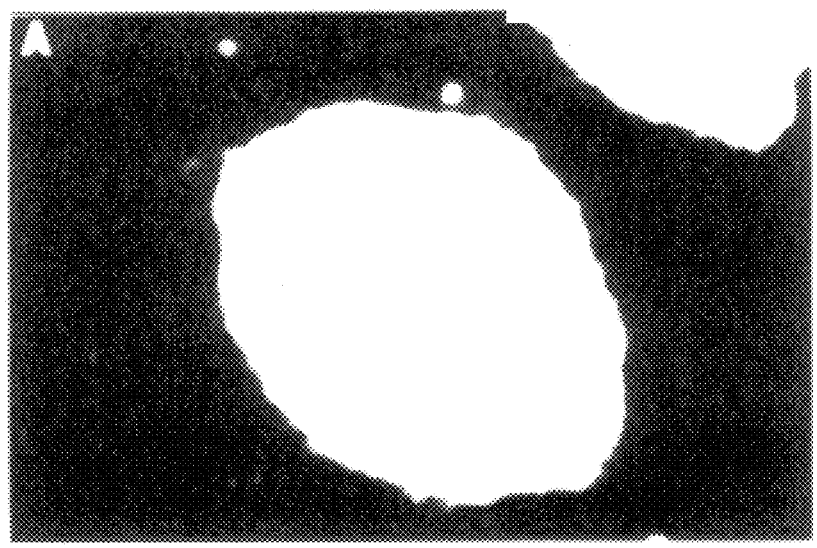
FIGS. 6A–6D: Intracellular localization of FITC-end labeled oligodeoxynucleotides (20 mers) in HeLa cells following DLS treatment. Cells were exposed to 2 $\mu$M FITC-labeled oligodeoxynucleotides for 24 hr (A, B) and the post-incubated in drug-free medium for 24 hr (C). Cells were treated with 2 $\mu$M free FITC-labeled oligodeoxynucleotides for 24 hr (D). Photographs represent computer-enhanced images from laser-assisted confocal microscopy. Magnification, ×320.
Figure 6B:
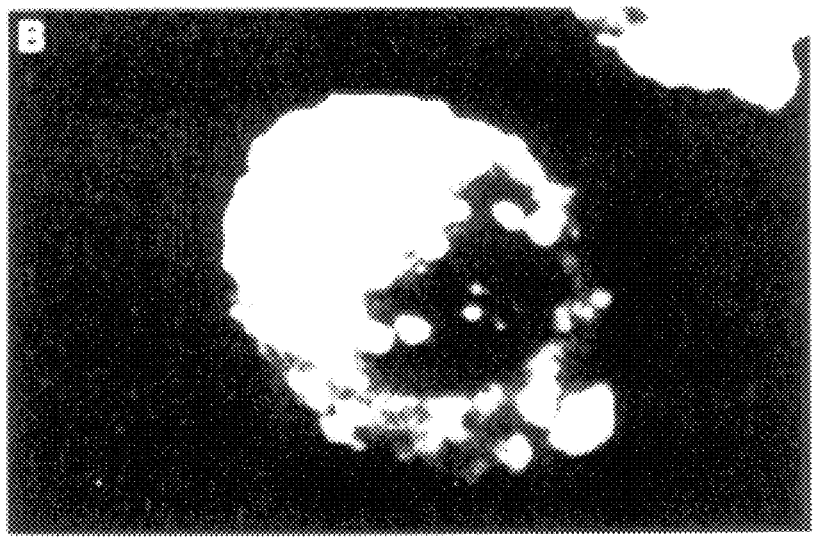
Figure 6C:
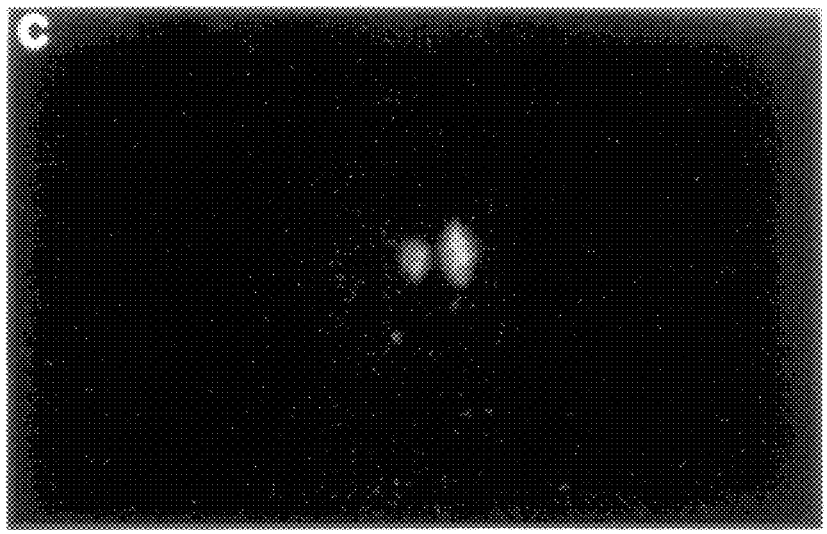
Figure 6D:
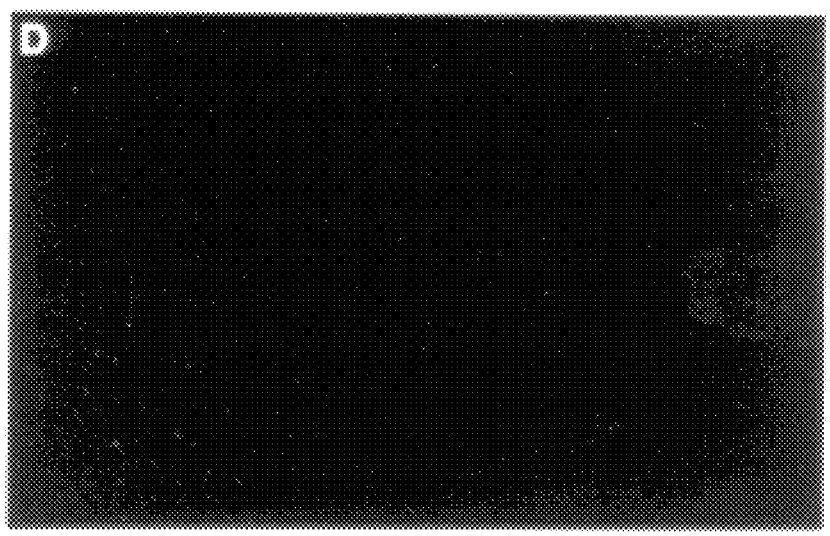

A high penetration of the labeled oligodeoxyribonucleotides was observed in all intracellular compartments (FIG. 6A). In order to investigate where oligodeoxyribonucleotides are highly concentrated, we significantly reduced the gain of the laser beam used for confocal microscopy observation of the same cell, and observed a punctuated intracytoplasmic distribution of the oligonucleotides (FIG. 6B). This suggests that DLS-liposomes transport oligonucleotides into cells via endocytosis and then oligonucleotides quickly escape from endocytic vesicles leading to a release of free oligonucleotides in the cytoplasm. Oligonucleotides are immediately transported from the cytoplasm to the nucleus (FIG. 6C). An extremely weak fluorescence intensity was observed in cells incubated with free labeled oligonucleotides, suggesting poor penetration and/or degradation by nucleases present in the serum-containing culture medium (FIG. 6D).

This observation is of great interest since it shows efficient delivery of nucleic acids to cells, total and immediate escape from endocytic vesicles where active degradation could take place, and nuclear localization after cell treatment. Theoretically, cell delivery of plasmid-DNA via DLS-liposomes may use the same pathway of cell internalization.

EXAMPLE 7

Preparation of a DOGS/DOPE Containing Liposome Composition with Adenovirus Particles The adenovirus strain used in the present invention is the dl 312 strain received as a gift from T. Shenk (Princeton Univ., Princeton, N.J.). Any adenovirus strain can be used in the present invention. Preparation of adenovirus capsids (no DNA) using cesium chloride gradient method may be performed following adenovirus collection and preparation. Whole adenovirus particles (with DNA) but inactivated by UV irradiation (10 J.m$^{-2}$ 8-1) may also be used. Hydrophobic binding of adenovirus to the liposomes is carried out by simply mixing the liposome suspension with the adenovirus concentrate. For example, particles equivalent to $10^8$ PFU (Plating Forming Unit) are added to 12.5 μl of a DLS-liposome-associated DNA preparation corresponding to 1 μg DNA and 12.5 μg lipids. The mixture is slightly homogenized and then incubated at 37° C. for 1 hr with gentle shaking. Immediately after incubation adenovirus-DNA liposome preparation is added to cell culture. Transfection procedure is the same as that used for DLS liposomes.

FIG. 7 illustrates that adenovirus associated liposomes greatly enhance transfection efficiency in HeLa cells by a factor 4.5. Transfection efficiency obtained after simultaneous addition in cell culture medium of liposomal DNA and adenovirus particles at equivalent concentration was significantly lower (2.7-fold). This demonstrates the specific additional effect of the adenovirus particle attachment to the liposomes on gene expression and particularly on the plasmid DNA escape from endocytic vesicles.

EXAMPLE 8

Transmission Electron Microscopy Comparison of Lipidic Particles and DLS-Liposomes DLS-liposomes and Transfectam™ (Promega, WI) reagent (DOGS) samples were submitted to negative staining and Transmission Electron Microscopy (TEM) analysis. The following is a part of the observations independently made by ABI Inc (Columbia, Md.).

DLS-liposomes: "Lipidic particles were observed throughout this preparation and were found in large quantities." "Each different particle appeared to display a heavily stained core region, which was surrounded by many different layers of membranes or envelopes. The particles contained so many different layers of membranes, it was difficult to establish the size of one lipidic particle to the next. Although it was difficult to measure the overall size of the particles, due to their pleomorphic shape and varied number of layers, it appeared the particles ranged from 200 to 3000 nm in diameter. The grid areas showed a high concentration of smaller lipidic particles throughout the background of the sample".

Transfectam™ reagent (DOGS): "Possible lipidic particles were found in this sample, in small quantities. The particles found in this sample were very different from those observed in the previous sample. The lipidic particles observed appeared to be either in the process of breaking down or they had never properly been formed. Large areas of lipid-like material were observed, however, they did not display any ultrastructural detail, such as different layers of membranes. The only similarity between this sample and the previous sample was that the lipidic particles were heavily stained. Very little debris was found in the background of the sample."

Thus, TEM analysis as demonstrated that DLS-liposomes are bilayer membranes vehicles. This specific ultrastructure differentiates DLS-liposomes from the Transfectam™ reagent or other cationic liposomes thus far commercialized, such as Lipofectin™ (BRL Co., ND). These nonliposome particles, when complexed with DNA do not form membrane bilayer-containing vesicles but rather are lipid coating particles that presumably contain nucleic acids. Thus they are not be liposomes in the true sense of the term. DLS-liposomes provide better efficacy in transferring DNA which can be explained by their liposomal structure. Furthermore, we may expect improved pharmacokinetic properties such as increased plasmid half life. In addition, the presence of a membrane bilayer in DLS-liposomes makes possible the anchorage of antibody to their surface which may result in cell targeting.

EXAMPLE 9

Expression of the MDR-1 Gene in Cultured Murine Bone Marrow Cells

The MDR-1 gene expresses the P-glycoprotein ("P-gp"), a plasma membrane protein involved in the emergence of the Multi-drug Resistance phenotype which may occur after chemotherapy. The MDR-1 gene was used in this example as a marker of gene delivery in order to assess the efficacy of bone marrow transplant of MDR-1 gene transfected bone marrow cells by DLS-liposomes, both DLS-1 and DLS-2.

In order to assess the efficacy of bone marrow transplantation for "ex vivo" gene therapy, murine bone marrow cells were transfected with this plasmid and the DLS-liposomes and transplanted into Balb-C mice. The proliferation and differentiation of transduced hematopoietic progenitor cells were detected up to 21 days after transplantation in the spleen and the bone marrow, suggesting that the bone marrow transplant had taken place.

Murine bone marrow cells were harvested and quickly transfected with the pHaMDR GA plasmid encapsulated in DLS-liposomes. Seven different experiments have confirmed that the MDR-1 gene was expressed in bone marrow cells since cells continue to grow under selective pressures (vincristine). In addition, lymphocyte, macrophage and fibroblast populations have been shown to exhibit the MDR phenotype after selection (using the rhodamine drug efflux method).

EXAMPLE 10

In vitro and in vivo Transfection of BMC

In order to achieve efficient liposomal transfection, both ex vivo and in vivo approaches have been used. The protocols shown in FIG. 1 were utilized. In examples 10–13, DLS-liposomes-2 are used. 1) the in vitro/ex vivo approach, in which mice were pre-treated with 5-fluoro Uracil ("5-FU") (150 mg/kg) by the method described in Hodgson et al. (1979 Nature 281:381–2) were sacrificed, and their bone marrow cells ("BMC") were transfected with 10 μg of DLS/MDR in T25 culture flasks (Costar). BMC transfected with DLS/Neo was used as negative controls. After 4–5 days, BMC were transplanted into lethally irradiated mice. Some BMC were kept for analysis by FACSort, PCR or kept in suspension culture with or without vincristine for 48 hours after which they were tested in semisolid medium for their potency to form colonies. 2) The direct in vivo gene delivery approach was used, in which 2–3 days after being pre-treatment with 5-FU (150 mg/kg), mice were injected intravenously with 75 μg DLS/MDR. All negative control mice were injected with DLS/Neo.

Mice from both groups were sacrificed at different time points, and hematopoietic cells were collected for analysis by PCR, FACSort, or assayed in methylcellulose for the potential to form colonies in the presence of different concentrations of vincristine.

Mouse peripheral blood (PB) was obtained by eye bleeding. Mouse BMC were obtained by flushing the long bones with DMEM using a 21 gauge needle. Spleen cells were obtained by pressing the spleens with the barrel of a 3 cc syringe.

Bone marrow transplantation ("BMT") procedure

To assess functional expression of P-gp, $1 \times 10^6$ transfected cells and control cells were incubated in FACSort medium containing 1 μg/ml rhodamine 123 (rho123) (Sigma) at 37° C. for 15 minutes. After washing, the cells were transferred into rho123 free medium at 37° C., and incubated for 3–4 hours. The cells were then washed and analyzed by FACSort. Results were displayed as histograms, where efflux of rho123 would be registered as a decease of fluorescence intensity.

Mouse Bone Marrow Cell Culture

Bone marrow cells (BMC) were harvested from 6–12 weeks old C57B1/6 mice purchased from Frederick Research Laboratories (Frederick, Md.), and housed in a specific pathogen-free environment. Mouse BMC culture was carried out in DMEM supplemented with 50 μg/ml penicillin/50 μg/ml streptomycin, 2 mM glutamine (Gibco laboratories, Greenbelt, Md.), and 10% calf serum (Colorado Serum Company, Denver, Colo.). Cell growth factors mouse Il3 9100 ng/ml), human Il6 (200 ng/ml) (Collaborative Science Inc.), and rat SCF (10 μg/ml) (generously provided by Amgen, San Diego, Calif.) were added to the media before each experiment.

Plasmids

The MDR1 retroviral expression plasmid, pHaMDR1/A containing wild type human MDR1 cDNA under transcriptional control of the Harvey Murine Sarcoma Virus-Long Terminal Repeat (Ha-MSV-LTR) sequences has been described (Pastan, et al. 1985 PNAS 85:4486–90). A plasmid containing the neomycin resistance gene wit the same promoter sequence as pHaMDR1/A was used as negative control (pHaNeo) (Zhu et al. 1993 Science 261:209–11).

Liposomes were formed by dissolving in chloroform 1 mg spermine-5-carboxy-glycinedioctadecylamid (DOGS) and 1 mg of the neutral lipid DOPE (0.5:1, molar ratio) designated further as DLS. After stirring by gentle vortexing, the mixture was evaporated to dryness. The subsequent dried lipid film was resuspended in a minimal volume (7 ml/mg lipid) of water containing plasmid (1.4 mg/ml). Formulation of DLS was carried out by thorough stirring. Entrapment and/or assimilation of the plasmid by the DLS is efficient and nearly complete. pHaMDR1/A, and pHaNeo plasmids entrapped in DLS were identified respectively as DLS/MDR, and DLS/Neo.

Polymerase Chain Reaction

Total genomic DNA from in vitro transfected BMC, as well from different hematopoietic cells collected from transplanted and in vivo transfected mice, was obtained using a DNA extract kit (Gentra systems, Inc., Research Triangle Parc, N.C.). The DNA yield and purity were tested by UV spectroscopy. PCR was carried out with 1 μg total DNA, 1 unit of AmpliTaq Polymerase and reaction kits (Perkins Elmer, Roche, Branchburg, N.J.) in a final volume of 100 μl. Each cycle of PCR included a 1 minute step of denaturation at 95° C., a 1 minute step of primer annealing at 57° C., and a 1 minute step of extension/synthesis at 72° C. The presence of human MDR1 gene specific sequence were probed by using a set of primers described in Noonan et al. (1990 PNAS 87:7160–4) yielding a product size of 167 bp. Each primer was added at 40 pmol per reaction. PCR products were separated on a 2% agarose gel and stained with ethidium bromide.

Selection of BMC in suspension culture $3 \times 10^6$ BMC were added to BMC culture medium containing 30 ng/ml vincristine (Sigma). Cells were left for 48 hours in culture after which floating cells were collected and pooled with adhering mouse BMC that were detached using cell scrappers. Cell were counted on a hematocymeter and viability was established by trypan blue exclusion.

Transfer of MDR1 in gene BMC after transfection using DLS Liposomes

Figure 8:
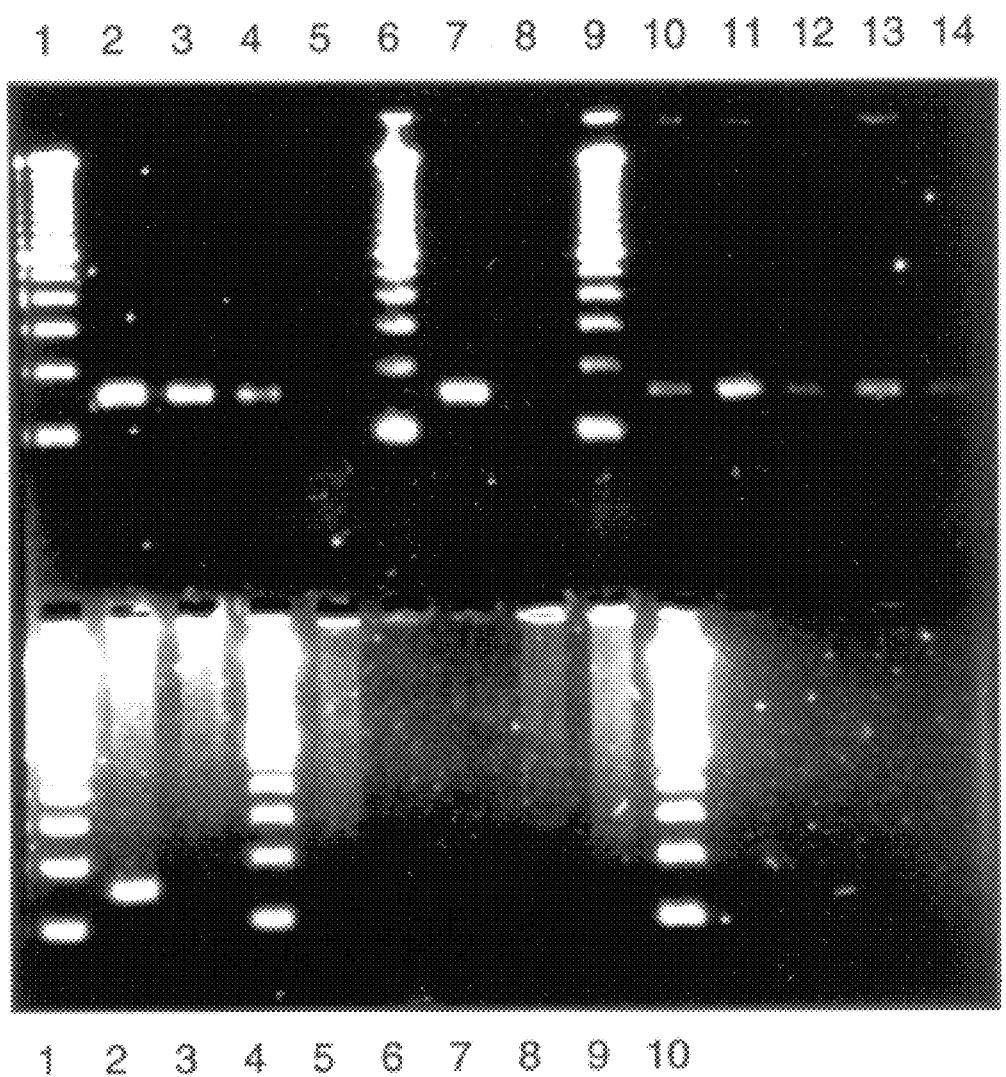
FIG. 8: PCR of genomic DNA extracted from different hematopoietic cells transfected in vitro/ex vivo and in vivo. Product size was assessed by comparison with a 100-bp ladder run in parallel (upper row: lanes 1, 6, 9; lower row: lanes 1, 4, 10). Upper row: lane 2 pHaMDR1 positive DNA control; lane 3, genomic DNA from NIH3T3-MDR1 transfected, colchicine resistant cells; lane 4, DNA from NIH3T3 cells transfected with MDR1 using the calcium phosphate precipitation protocol, but not selected in drug; lane 5, DNA from NIH3T3 parental cells; lane 7, BMC transfected 4 days in vitro with DLS/MDR and selected in vincristine for 48 hours; lane 8, BMC transfected with DLS/Neo; lanes 10, 11, 12 show, respectively, BMC, spleen, and PB cells 15 days after treatment of a mouse with i.v. injection of DLS/MDR1; lanes 13 and 14 show BMC and spleen cells from a mouse transplanted with BMC transfected in vitro with DLS/MDR1, 15 days post-BMT. Lower row: lane 2, MDR1 positive BMC from a mouse transplanted 30 days earlier, lane 3, BMC from a control DLS/Neo recipient mouse; lanes 5, 6, 7, BMC, spleen cells, and PB cells respectively from a DLS/Neo i.v. transfected mouse; lanes 8, 9, BMC, and spleen cells respectively from a transplanted mouse with DLS/Neo transfected BMC.

To assess the transfer of the human MDR1 gene in DLS/MDR transfected murine cells, genomic DNAs from different NIH3T3 and hematopoietic cells were tested by PCR. Successfully transfected cells gave an amplified product of 167-bp as shown with positive controls pHaMDR1 (FIG. 8, upper row, lane 2), NIH3T3 colchicine resistant cells (FIG. 8, upper row, lane 3), and NIH3T3 cells transfected with the human MDR1 cDNA using the calcium-phosphate precipitation method (FIG. 8, upper row, lane 4). A positive band was obtained with in vitro DLS/MDR transfected BMC that were selected for 48 hours in 30 ng/ml vincristine (FIG. 8, upper row, lane 7). FIG. 8 shows representative positive samples that were obtained from mouse hematopoietic tissues. Positive bands were detected in BMC, spleen, and PB cells (FIG. 8, upper row, lanes 10, 11, 12 respectively) of an DLS/MDR in vivo treated mouse, 15 days after i.v. injection; as well as in BMC and spleen cells (FIG. 8, upper row, lanes 13, 14 respectively) of a reconstituted mouse, 15 days post-BMT with DLS/MDR1 transfected BMC. The MDR1 gene was still detected in BMC 30 days post-transplantation in the one mouse tested (FIG. 8, lower row, lane 2). None of the control animals DLS/Neo i.v. transfected (FIG. 8, lower row, lane 5, 6, 7; BMC, spleen cells, and PB cells respectively), or transplanted with DLS/Neo transfected BMC (FIG. 8, lower row, lanes 8, 9: BMC, and spleen cells respectively) showed any positive band 15 days post-transfection nor 30 days post-BMT (FIG. 8, lower row, lane 3: BMC).

In DLS/MDR in vivo treated mice, specific band for the human MDR1 was detected in 5 of 6 BMC samples, 4 of 5 spleen cells, and 4 of 7 PB cells tested. BMC from one in vivo treated mouse gave a positive band when analyzed 28 days post-i.v. injection with DLS/MDR. In the group of transplanted mice, human MDR1 specific band was detected in 3 of 4 BMC, 2 of 3 spleen cells, and 2 of 2 PB tested cells. All in vitro transfected BMC turned out positive for human MDR1 whether before or after being drug selected (4 of 4 and 2 of 2 respectively).

EXAMPLE 11

In vitro DLS/MDR Transfection Leads to Expression of P-gp in BMC

Figure 9A:
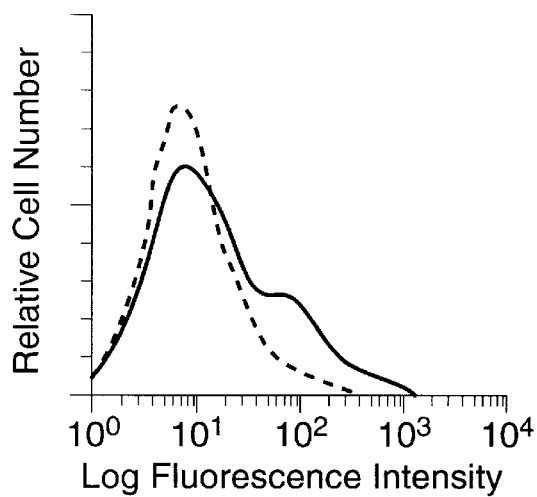
FIGS. 9A and 9B: FACSort analysis of BMC taken after in vitro DLS/MDR transfection, before (A), and after (B) selection for 48 hours in 30 ng/ml vincristine. The figure represents two histograms generated by FACSort analysis of BMC stained with MRK16 (plain line) or G2CL (dotted line), and GαM IgG-FITC. Displayed on the X axis is the fluorescence intensity on a logarithmic scale, and on the Y axis is the relative cell number.
Figure 9B:
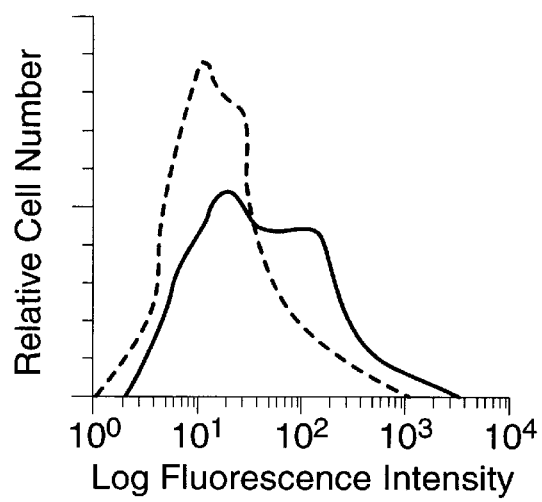

Transfection of mouse BMC with DLS/cDNA for 4–5 days did not affect the morphology nor the number of cells collected when compared with the untransfected BMC control. However, when the cells were subjected to selection with 30 ng/ml of vincristine for 48 hours, the numbers of viable cells obtained varied greatly. From a total of $3 \times 10^6$ cells plated before the selection pressure was added, only $1.5 \times 10^4$ cells, and $2 \times 10^4$ viable cells were counted in the untransfected, and in the DLS/Neo transfected control cells respectively. In contrast, $2 \times 10^6$ cells remained viable in the DLS/MDR transfected BMC. Using the human P-gp specific monoclonal antibody MRK16, and G2CL monoclonal antibody as an irrelevant negative control antibody, FACSort analysis was performed of DLS/MDR transfected BMC not subjected (FIG. 9A and subjected to selection with 30 ng/ml of vincristine for 48 hours (FIG. 9B). The histogram in FIG. 9A shows that after transfection, MRK16 monoclonal antibody stained 15% of the cells positively above the background fluorescence level. Moreover, the whole histogram representing BMC stained with MRK16 monoclonal antibody appeared positively displaced when compared to the histogram representing the cells stained with G2CL monoclonal antibody. Positive staining was noted each time the analyzed was done (5 of 5).

Figure 10:
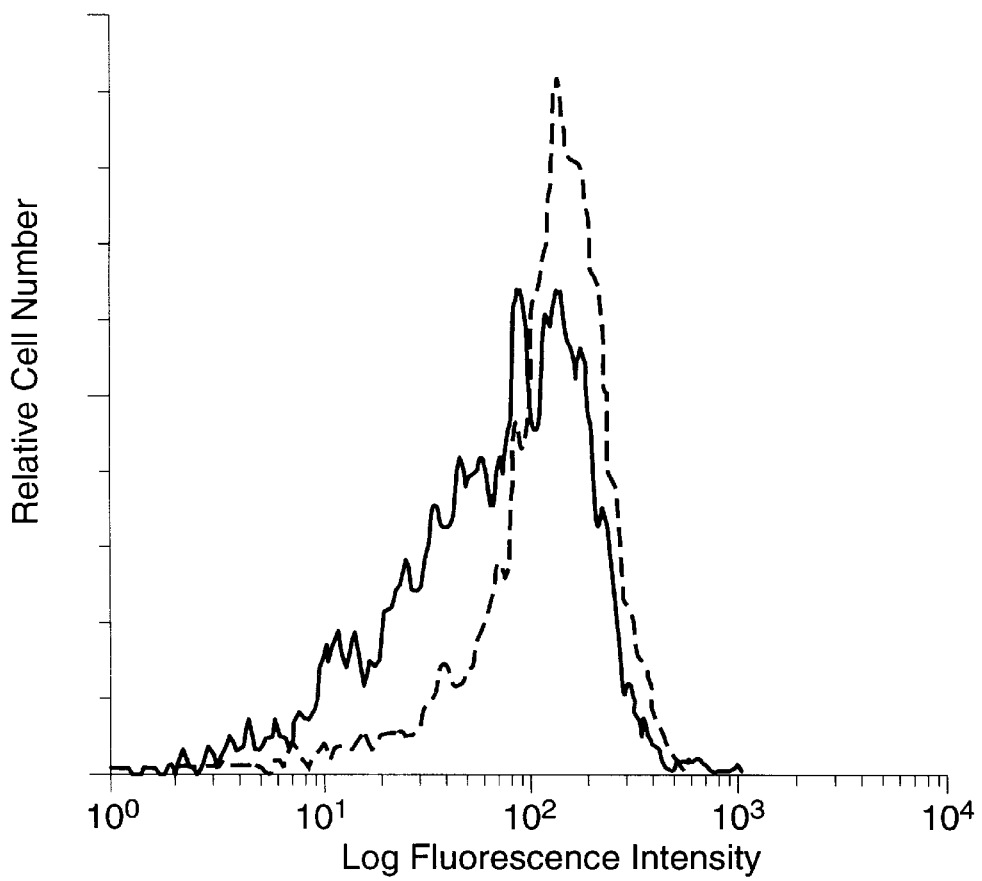
FIG. 10: Accumulation of rho123 after DLS/MDR, or DLS/Neo transfection without selection. BMC transfected in vitro for 5 days with DLS/MDR (plain line) compared to DLS/Neo (dotted line) three hours after exposure to rho123.
Figure 11A:
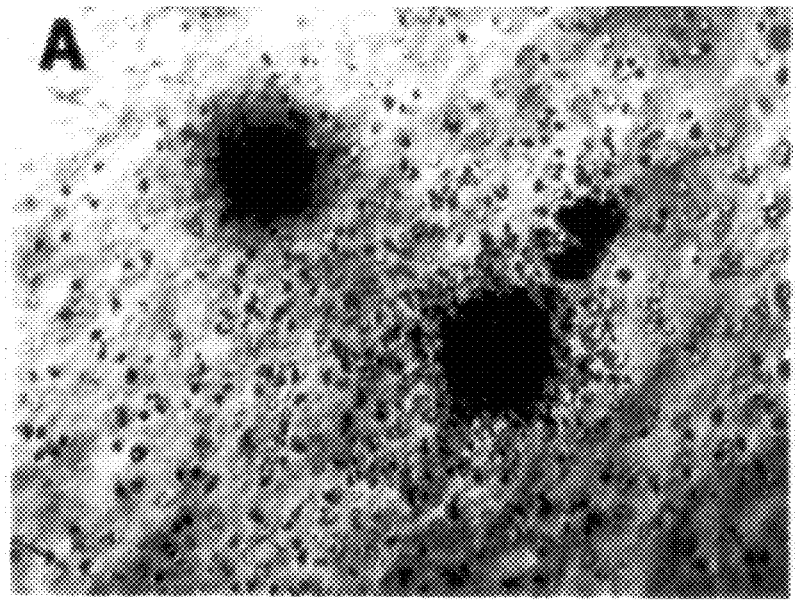
FIGS. 11A–11D: Appearance of CFU-Mix in methylcellulose obtained from the in vitro transfected BMC. Representative photographs of CFU-Mix at day 12 of culture are shown. Panel A shows two colonies grown from control DLS/Neo transfected BMC with no selection. Panel B shows two colonies grown from BMC transfected BMC with DLS/MDR with no selection. Panel C, shows the absence of colonies from transfected BMC with DLS/Neo with 20 ng/ml vincristine, and panel D shows colonies of BMC transfected with DLS/MDR 20 ng/ml vincristine selection, and from transplanted and in vivo treated mice.
Figure 11B:
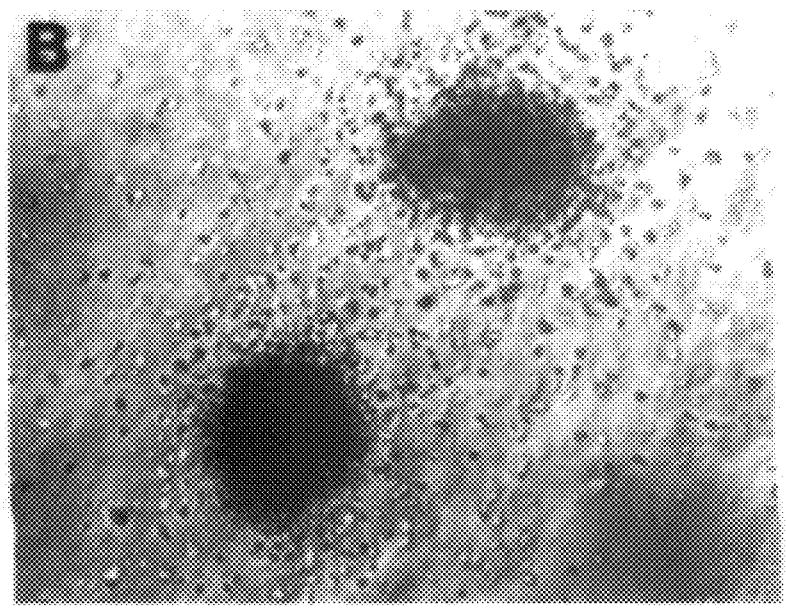
Figure 11C:
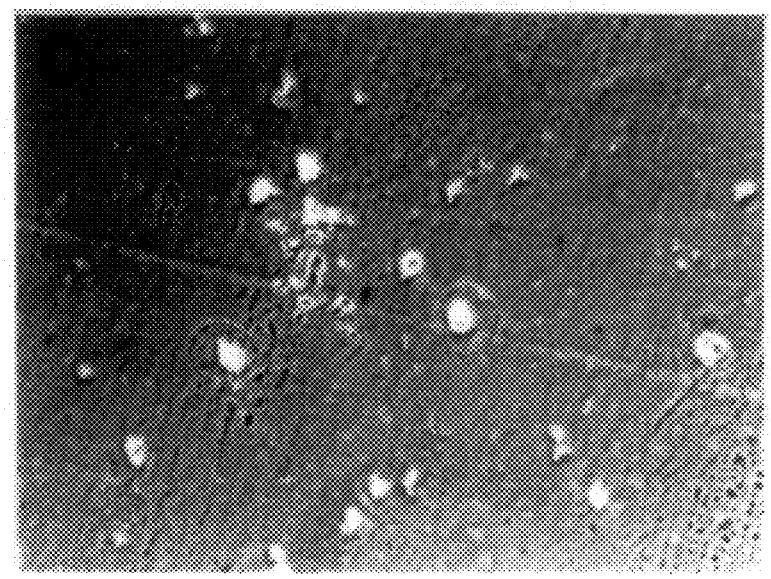
Figure 11D:
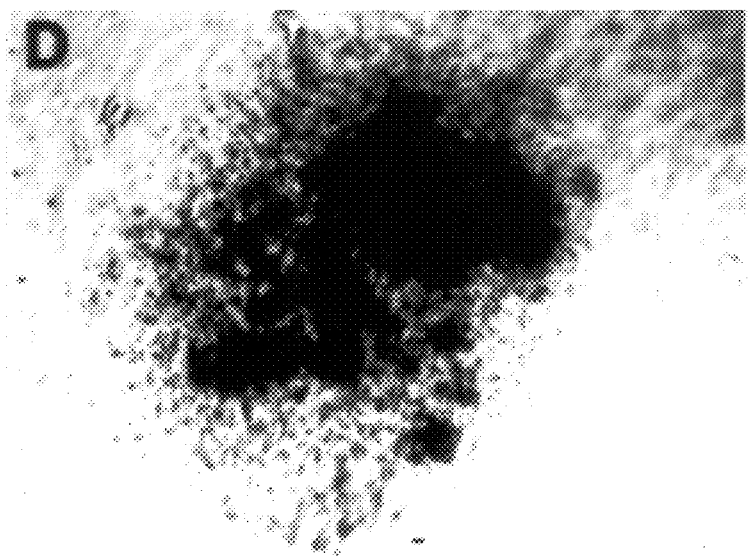

Using FACSort analysis, we demonstrated the function of the gene product in a rho123 efflux assay as early as 5 days post-transfection with DLS/MDR. As shown in FIG. 10, 3 hours after exposure to rho123 the fluorescence level of the non-selected in vitro DLS/MDR transfected cells was lower than that of the control BMC transfected with DLS/Neo.

Staining for P-gp expression

Collected cells were resuspended, washed in PBS (Gibco Laboratories) supplemented with 0.1% bovine albumin (Sigma) and incubated with MRK16 (generously provided by Hoecht-Japan), a mouse $IgG_2$ monoclonal antibody specific for an external epitope of the P-gp. As a negative control, G2CL (Becton Dickinson, Calif.), a mouse $IgG_{2a}$ monoclonal antibody was used. Non-specific binding to mouse cells were prevented by the use of 24G2, a rat anti-mouse Fc receptor monoclonal antibody (Pharmingen, San Diego, Calif.) that was incubated for 10 minutes prior to the addition of the MRK16 and G2CL. After a 30 minute incubation at 4° C., the cells were washed and incubated with a secondary goat anti-mouse IgG fluoro-iso-thiocyanate conjugated (GαM IgG-FITC) antibody for another 30 minutes at 4° C. After a final wash, the cells were analyzed using a FACSort (Becton Dickinson, Calif.), and fluorescence intensity levels were illustrated as histograms plotted against the X axis on a logarithmic scale, with the relative cell number displayed along the Y axis.

Colony forming unit assay in methylcellulose

An assay for hematopoietic progenitor cells able to form colonies (CFU-Mix) was performed using an established method (Wong et al. 1986 PNAS 83;3851–4). $1 \times 10^4$ BMC were plated in semisolid medium containing 0.9% methylcellulose (StemCell Technologies Inc., Vancouver, Canada), 10% calf serum, 1% serum, 1% glutamine, 1% penicillin, 1% streptomycin, 100 ng/ml mouse erythropoietin factor (Sigma), 100 ng/ml mouse II3, and 100 ng/ml mouse G-CSF (Pharmingen, San Diego, Calif.). In each experiment, all cells were plated in triplicate wells of a 96-well microtiter plate (Nunc). CFU-Mix that were clearly expended were enumerated using an inverted microscope after incubation at 37° C. in a humidified 5% $CO_2$ atmosphere for 10 to 12 days.

In vitro transfected BMC, were analyzed for their ability to form colonies in semisolid medium in the presence or absence of vincristine. Although conditions varied somewhat (these clonogenic assays were done with cells from three different in vitro transfection experiments), when no selection was applied there were typically between 10 to 18 CFU-Mix per $10^4$ total BMC plated. As in vitro controls, non-transfected or DLS/Neo transfected BMC were assayed. FIG. 11, panel A, represent typical colonies obtained from DLS/Neo transfected BMC. Their number and morphology was comparable to the colonies formed from untransfected and DLS/MDR transfected BMC (FIG. 11, panel B). When BMC clonogenic potential was tested under selective pressure of 20 ng/ml of vincristine, no colonies formed from the untransfected, nor from the DLS/MDR transfected BMC (FIG. 11, panel D). Table 1, panel A, shows absolute numbers of CFU-Mix obtained from $1 \times 10^4$ plated BMC.

TABLE 1

| A | normal BMC day 5 in culture not transfected | Neo BMC day 5 post transfection | MDR1 BMC day 5 post transfection |
|---|---|---|---|
| no selection | 17.8 ± 8.9 | 13.2 ± 8.3 | 12.1 ± 4.2 p-0.06 |
| 10 ng/ml vincristine | 13.4 ± 8.13 | 7.7 ± 7.1 | 9.8 ± 3.9 p = 0.3 |
| 20 ng/ml vincristine | 0 0% | 0 0% | 3.6 ± 2.6 p = 0.007 (29.7%) |

| B | normal BMC day 5 in culture not transfected, 48 hours preselection | Neo BMC day 5 post transfection, 48 hours preselection | MDR1 BMC day 5 post transfection, 48 hours preselection |
|---|---|---|---|
| no selection | 9.6 ± 9.9 | 5.4 ± 2.1 | 39.7 ± 9.2 p = 0.007 |
| 10 ng/ml vincristine | 3.8 ± 6.3 | 2.6 ± 1.3 | 33 ± 4.0 p = 0.000 |
| 20 ng/ml vincristine | 0.6 ± 1.1 6.25% | 0.7 ± 0.5 12.9% | 26.5 ± 7.4 P = 0.000 (66.7%) |

Under no selection, the number of colonies obtained from the untransfected, DLS/Neo transfected, and DLS/MDR transfected BMC were similar, with 17.8+/−8.8, 13.2+/−8.3, and 12.1+/−4.2 CFU-Mix respectively. When 10 ng/ml of vincristine was added to the methylcellulose, only 13.4+/− 8.13 CFU-Mix were counted from the untransfected, and 7.7+/−7.1 CFU-Mix were counted from the DLS/Neo transfected BMC. In contrast, 9.8+/−3.9 (p=0.3) CFU-Mix grew from the DLS/MDR transfected BMC. Most significant was the difference observed when the BMC were tested under 20 ng/ml of vincristine. No colonies grew from the untransfected, nor from the DLS/Neo transfected BMC, whereas 3.6+/−2.8 (p=0.007) of the DLS/MDR transfected BMC were able to form CFU-Mix. This indicated a efficiency of transfected of 29.70%.

After transfecting the cells in vitro, the cells were subjected to 30 ng/ml vincristine for 48 hours. This significantly enriched for the population of MDR1 positive progenitor cells, as shown in Table 1, panel B. Under no selection, 39.7+/−9.2 (p-0.007) CFU-Mix were counted from the DLS/MDR transfected BMC. Whereas, only 9.6+/−9.9 and 5.4+/− 2.1 colonies grew from the untransfected BMC, the number of CFU-Mix dropped slightly to 33+/−4.0 (p=0.000) and 26.5+/−7.4 (p=0.000) when 10 ng/ml or 20 ng/ml of vincristine was added respectively. This shows that 66.7% positive cells were selected by pre-selecting the transfected cells. In contrast, at 10 ng/ml vincristine the numbers of CFU-Mix in the untransfected and DLS/Neo transfected BMC dropped to 3.8+/−6.3 and 2.6+/−1.3 respectively, and at 20 ng/ml vincristine the numbers dropped to 0.6+/−1.1 and 0.3+/−0.5 respectively.

EXAMPLE 12

Figure 12A:
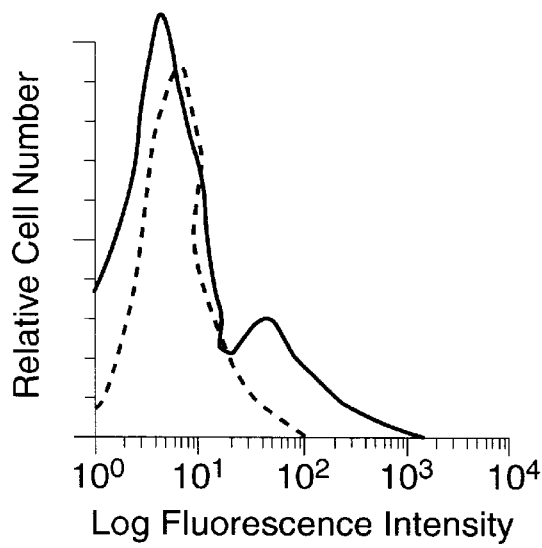
FIGS. 12A–12D: FACSort analysis of BMC taken from transplanted mice and from in vivo treated mice. The figure shows histograms generated by FACSort analysis wherein the X axis displays the fluorescence intensity on a logarithmic scale, and the Y axis displays the relative cell number. All histograms are generated after staining of BMC with MRK16 and GαM IgG-FITC antibody. Panel A and B show, respectively, histograms of BMC collected 15 days post-BMT and 25 days post-BMT. The recipient of DLS/MDR transfected BMC is shown as plain line, and recipient of DLS/Neo transfected BMC as dotted line. Panel C and D show, respectively, histograms of BMC taken 12 and 25 days post-i.v. injection of DLS/cDNA. The plain line shows the DLS/MDR treated animal, and the dotted line shows DLS/Neo transfected mice.
Figure 12B:
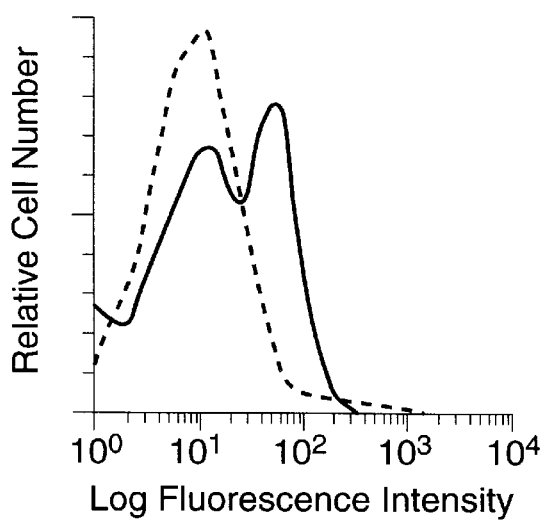

Transplantation of in vitro DLS/MDR transfected BMC and systemic delivery of DLS/MDR is followed by P-gp expression in mouse BMC Analysis of BMC obtained 5 days post-BMT from recipients of DLS/MDR transfected BMC showed no positively stained cells with MRK16, and GαM IgG-FITC antibody. However, 15 days post-BMT as shown on FIG. 12A, staining of DLS/MDR BMC from a transplanted mouse demonstrated higher levels of fluorescence than that of BMC taken from a mouse transplanted with DLS/Neo transfected cells, with 19.1% of the cells staining above the control levels. P-gp on BMC was still detectable by FACSort analysis 25 days post-BMT (FIG. 12B), with 21% of the cells staining positively in that mouse BMC.

Figure 12C:
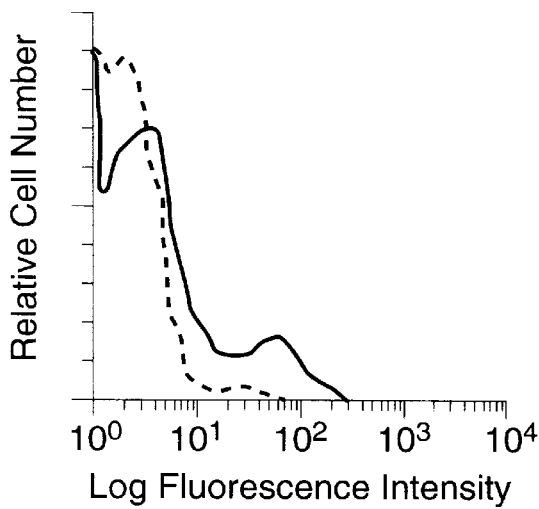
Figure 12D:
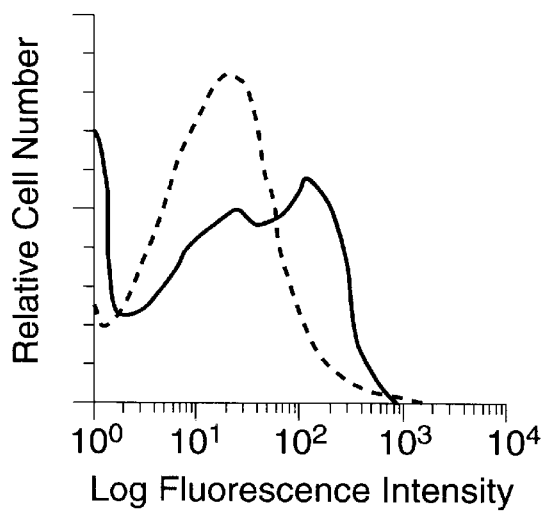
Figure 13A:
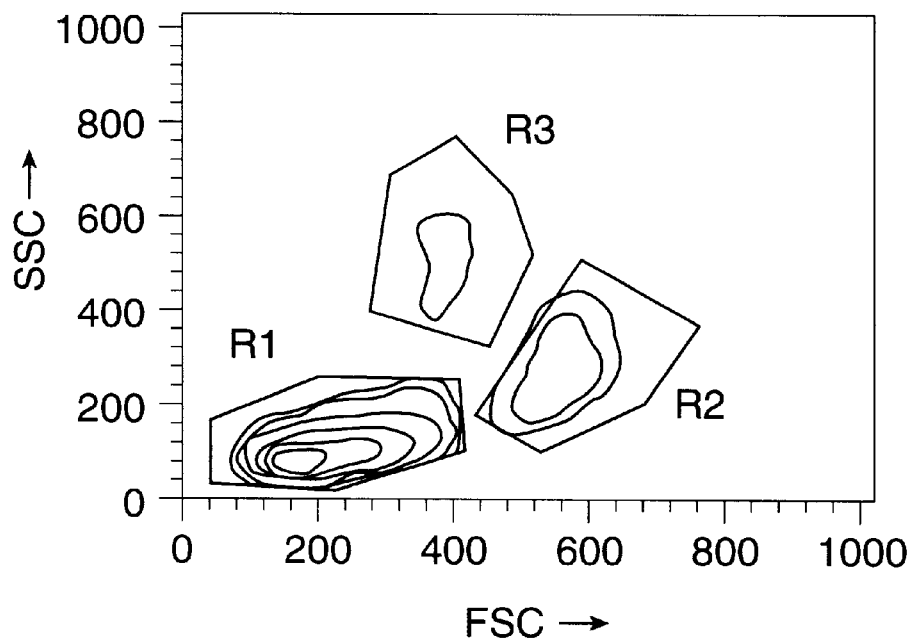
FIGS. 13A–13E: P-gp expression in BMC sub-populations taken from transplanted mice. The upper panels show the dot plot fluorescence representing the cell size as forward side scatter (FSC) on the X axis and cell density as side scatter (SSC) on the Y axis. On the left, DLS/Neo, and right, DLS/MDR are shown cells transfected BMC taken from mice 15 days after BMT. The lower panels shown the histograms of the different cell populations gated, and stained with MRK16 and GαM IgG-FITC. R1 shows the lymphocyte region, R2 shows the monocyte region, and R3 shows the granulocyte region. The staining of DLS/MDR transfected cells is drawn as a plain line, and staining of DLS/Neo transfected BMC is shown as dotted line.
Figure 13B:
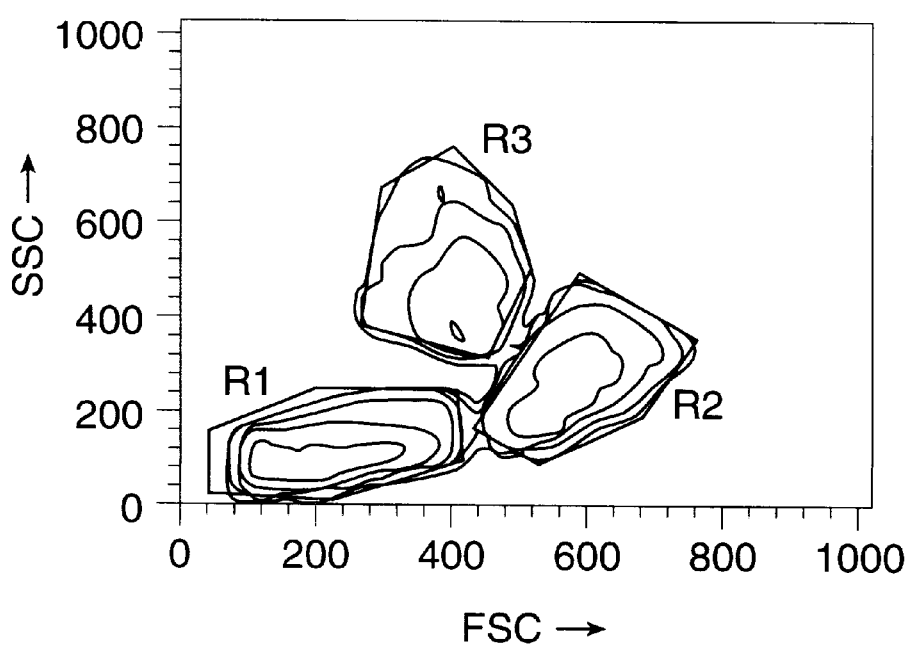
Figure 13E:
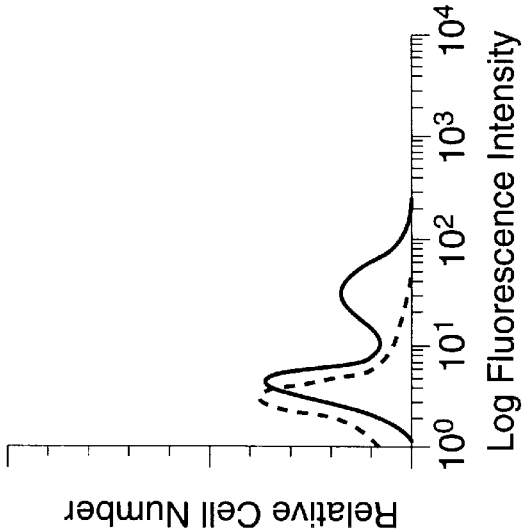
Figure 13D:
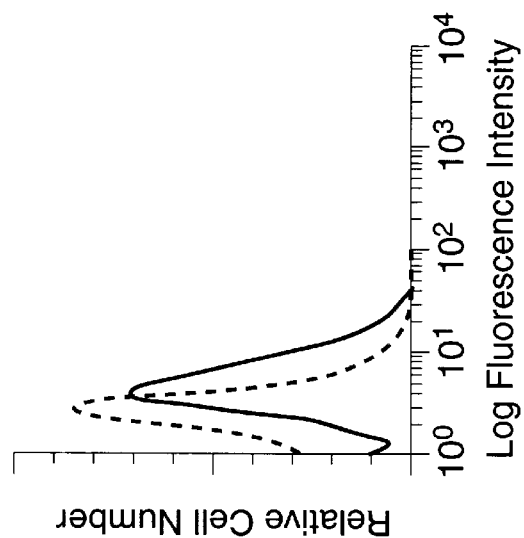
Figure 13C:
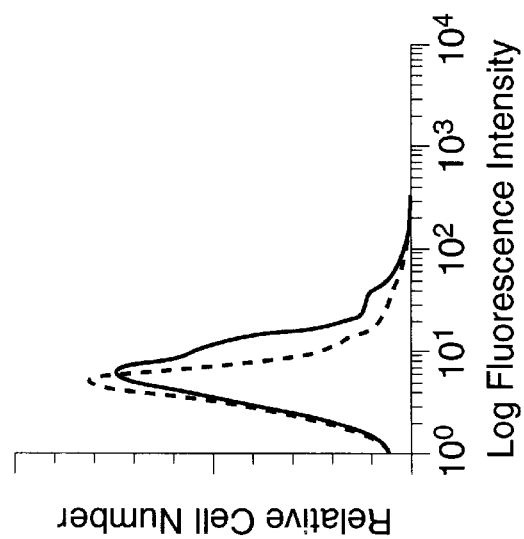
Figure 14A:
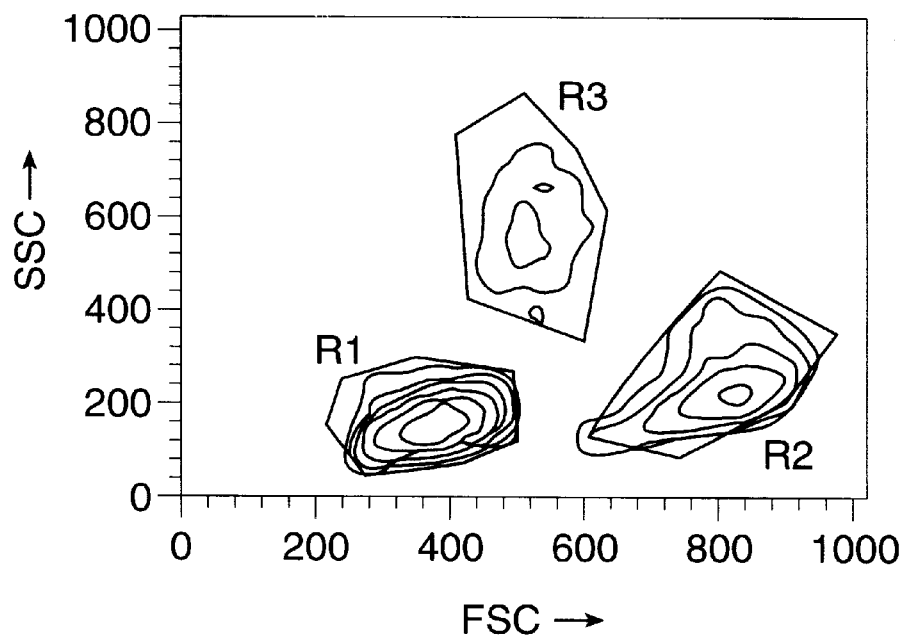
FIGS. 14A–14E: P-gp expression in BMC sub-populations taken from in vivo treated mice. The upper panel shows dot plot fluorescence: left, DLS/Neo, and right, DLS/MDR in vivo transfected BMC, 12 days post-injection. R1 shows the lymphocyte region, R2 shows the monocyte region, and R3 shows the granulocyte region. MRK16 staining of the different sub-populations of DLS/MDR transfected cells is drawn as a plain line, and staining of sub-populations of DLS/Neo transfected BMC are shown as a dotted line.
Figure 14B:
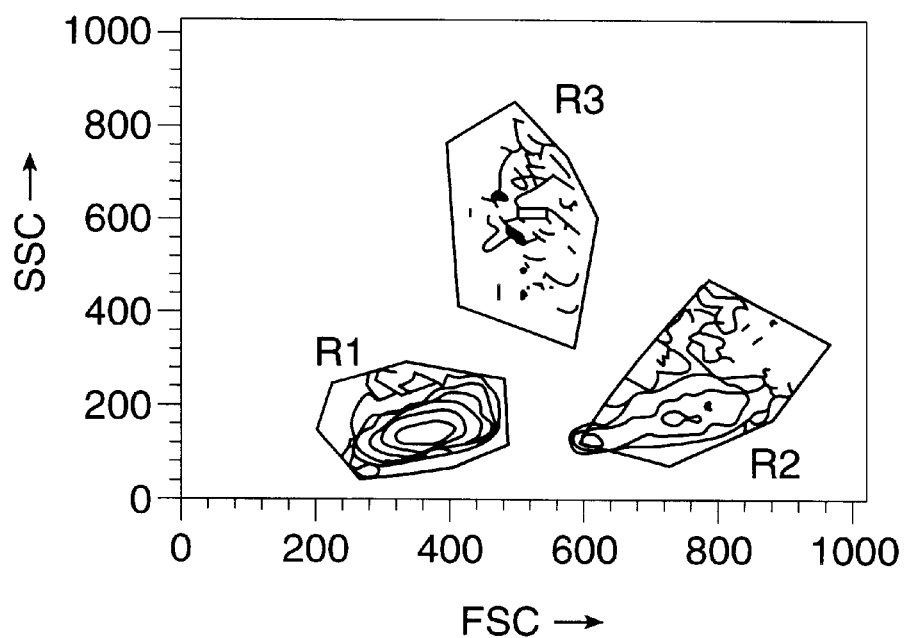
Figure 14E:
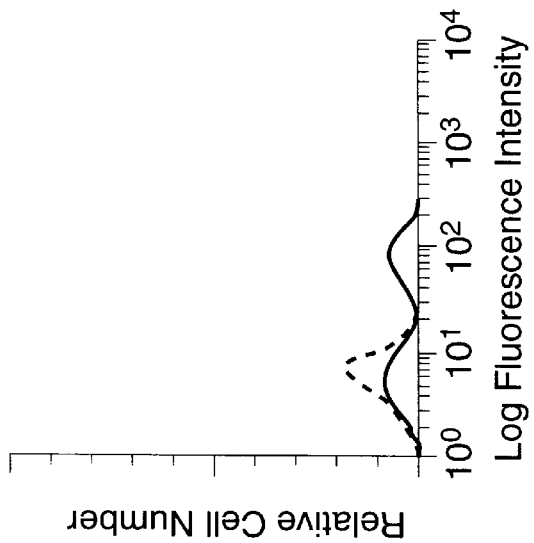
Figure 14D:
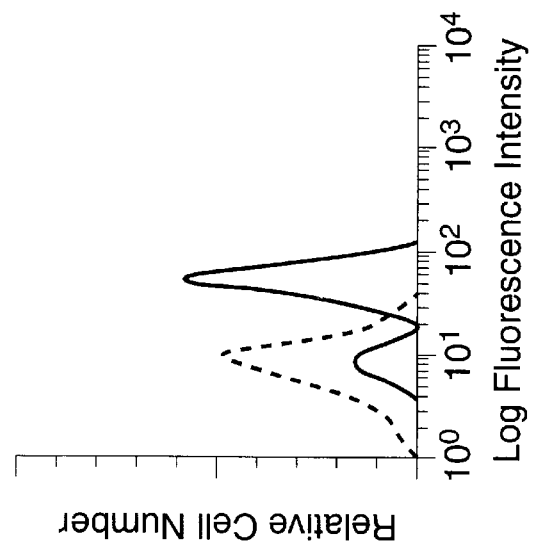
Figure 14C:
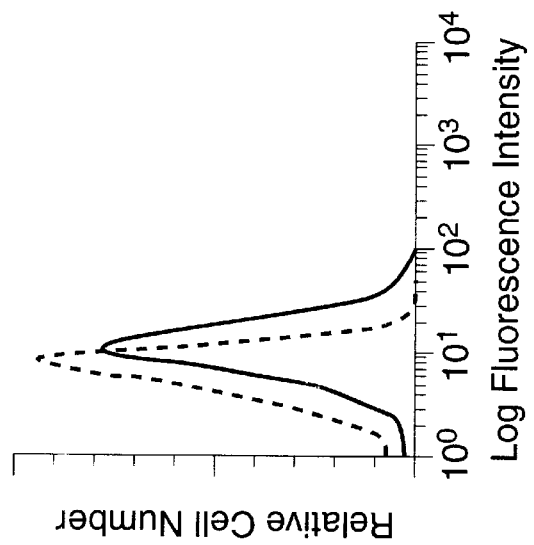

FIGS. 12C, and 12D represent data obtained by FACSort analysis of BMC from two DLS/MDR injected mice stained with MRK16, and GαM IgG-FITC 12 days (8 positive out of 9 tested), and 25 days (2 positive out of 2 tested) post-i.v. injection respectively. At both time points, BMC from DLS/MDR transfected mice demonstrated positive specific staining for P-gp when compared to the BMC obtained from DLS/Neo transfected mice. At day 12, DLS/MDR mouse cells stained positively (21.3i) compared to the DLS/Neo transfected mice. 25 days post-injection, 14.2% of the BMC stained positively.

EXAMPLE 13

P-gp expression in different BMC lineages after BMT and systemic delivery 15 days post-BMT, BMC were harvested from three mice, and analyzed for P-gp expression in different cell lineages. BMC were stained with MRK16 and GαM IgG-FITC. FIG. 13, top panel, shows a dot plot fluorescence representing cell size (FSC) plotted against cell density (SSC) that allowed us to differentiate three morphologically different population of BMC. Same cell distribution were seen in the DLS/Neo FIG. 13, (left), and the DLS/MDR FIG. 13, (right) transfected BMC: the lymphocytes shown as small sized cells of low density (R1), the monocyte as large sized cells of intermediate density (R2), and the granulocyte as intermediate sized cells of high density (R3). By gating each sub-population, the respective MRK16 fluorescence was observed (FIG. 13, lower panel). The FACSort data revealed that in each sub-population, namely the lymphocytes, the monocyte, and the granulocyte, most of the cells expressed P-gp.

Similar results as in the transplanted mice were found after analysis of BMC obtained from in vivo transfected mice 12 days post-i.v. injection (FIG. 14). When populations of BMC were transfected, all three hematopoietic cell populations gated, namely the lymphocytes (R1), the monocyte (R2), and the granulocyte (R3) specifically stained with MRK 16 when compared to the background DLS/NEO injected control BMC.

BMT with DLS/MDR transfected BMC and in vivo treatment with DLS/MDR leads to P-gp expression in hematopoietic progenitor cells At several time points after reconstitution the presence of drug resistant clonogenic progenitor hematopoietic cells were tested (two or three bone marrow transplanted mice from each group were tested at each time point). The results are presented in Table 2, panel A, representing the means values +/− standard deviation of colonies obtained with 20 ng/ml vincristine.

TABLE 2

| A | 4 days post-BMT | | 10 days post-BMT | | 15 days post-BMT | | 31 days post-BMT | |
|---|---|---|---|---|---|---|---|---|
| | Neo | MDR | Neo | MDR | Neo | MDR | Neo | MDR |
| 20 ng/ml vincristine | 0 | 0 | 0 | 0 | 1.4 ± 1.7 | 5.8 ± 2.4 $p = 0.0000$ | 0 | 2.5 ± 0.7 $p = 0.1$ |

| B | 4 days post-injection | | 10 days post-injection | | 21 days post-injection | | 36 days post-injection | |
|---|---|---|---|---|---|---|---|---|
| | Neo | MDR | Neo | MDR | Neo | MDR | Neo | MDR |
| 20 ng/ml vincristine | 0 | 0 | 0 | 13.9 ± 3.3 $p = 0.1$ | 0 | 7.7 ± 5.0 $p = 0.1$ | 0 | 2.4 ± 2.1 $p = 0.04$ |

With no drug selection added, BMC from DLS/Neo, and DLS/MDR BMT mice contained similar numbers of CFU-Mix (i.e.: at day 15 post-BMT, Neo: 22.7+/10.4, and MDR: 27.3+/−3.5). At 20 ng/ml vincristine, no colonies grew on day 4, or day 10 post-BMT from any DLS/Neo, or DLS/MDR recipient mice. Still, the results indicate that the transfection efficiency of 8.80 is real.

Injected mouse BMC, was also analyzed for its ability to form colonies in semisolid medium in the presence or absence of vincristine at different time points post-injection. As controls, DLS/Neo injected mice were assayed. With no drug selection added, BMC from DLS/Neo, and DLS/MDR injected mice contained similar numbers of CFU-Mix (i.e.: at day 21 post-DLS/MDR and DLS/Neo injection, 47.8+/−21.5, and 59.4+/−24.3 CFU-Mix were counted respectively; at day 36 post-injection, 30+/−12.1, and 28.2+/−6.3 colonies were counted in the DLS/MDR, and DLS/Neo injected mice had no CFU-Mix at days 4, 10, 21 and 36 post-treatment respectively. In contrast, the DLS/MDR treated mice, that grew no colonies at day 4 post-injection, had 13.9+/−3.3, 7.7+/−5, 2.4+/−2.1 CFU-Mix, at day 10, 21, and 36 post-injection respectively. The difference was significant (p, <0.05) only for the value taken at day 36, indicated an actual transfection efficiency of 8%.

EXAMPLE 14

In vivo administration of DLS-liposomes into Balb-C mice.

Plasmid DNA. Firefly "*Photinus pyralis*" peroxisomal luciferase gene (luc) was used as a report gene for the monitoring of transgene expression levels. In preliminary studies episomal vectors were constructed containing a genomic fragment of the human papovavirus, BKV. This fragment included the BKV viral early region and origin of replication, the large T antigen, and later viral capsid proteins. Sequence encoding the firefly luciferase (luc; 1.7 kb Bam HI-Sal I fragment of PGEM-luc [Promega]) gene was inserted under the control of the Rous sarcoma virus (RSV) promoter and the polyadenylation signal and transcriptional termination sequences from SV40. The resultant episomal/ reporter expression vector was termed pBKd1RSv-luc. For subsequent studies, a modified BKV plasmid containing the luc gene was constructed in which the entire sequences coding for the late BKV capsid proteins (VP1, VP2 and VP3) (Seif, I. et al. (1979) Cell 18, 963–977) were deleted to remove the expression of these potentially immunogenic proteins. The resultant episomal/reporter expression vector was termed pBKd2RSV-luc. In addition, a second series of pBKd1 and pBKd2 vectors were made in which luc expression was placed under the control of the enhancer/promoter sequences from the immediate early gene of the human cytomegalovirus (CMV) and the polyadenylation signal and transcriptional termination sequences from the bovine growth hormone gene. The resultant episomal/reporter expression vectors were termed pBKd1CMV-luc and pBKd2CMV-luc, respectively. The non-episomal pRSV-luc containing luc under the control of the RSV long terminal repeat was constructed as previously reported (DeWett, J. et al. (1987) Mol. Cell. Biol. 7, 725–737). pCMVintlux plasmid encodes the luc under the control of human CMV immediate-early promoter with intron A (Manthorpe, M. et al (1993) Hum. Gene Ther. 4, 419–431).

Preparation of the DLS Liposomes. Liposomes were formed by mixing 1 mg dioctadecyl-amidoglycyl spermidine and 1 mg dioleoyl-phosphatidyl ethanolamine. After thorough stirring, the mixture was evaporated to dryness in a round-bottomed borosilicate tube using a rotary vortex evaporator under vacuum. Then the dry lipid film was hydrated with a maximum volume (60 µl/mg lipid) of a solution containing 160 µg plasmid DNA and was slightly vortexed. After incubation at room temperature for 15 min, the resulting suspension was vigorously mixed by vortex. Subsequent liposomal DNA preparation was then diluted in 150 mM NaCl, and kept at 4° C. Liposomes appeared to range from 200 to 3,000 nm in diameter as determined by transmission electronic microscopy. DLS liposomes consist of multilamellar bilayers vesicles which may complex as well as encapsulate DNA. The entrapment rate was found to be 88±8% (mean ±S.D.) of the initial DNA input dose. This type of liposomes were used in examples 14–17.

In Vivo Gene Transfer. Plasmid-DNA in DLS-liposomes-2 liposome was administered by a single injection of 100 to 600 µl total volume in the tail vein of 4–6 week old female Balb/C mice. Control mice received 150 mM NaCl solution. Mouse tissues were collected in 2 ml Eppendorf tubes, quickly frozen on dry ice and stored at −70° C. until examined.

Plasmid vector containing the luciferase gene as a marker gene were delivered by DLS-liposomes in Balb-C mice. Various formulations of liposomes encapsulated plasmid at various DNA/lipid ratios were assayed. In these experiments transgene expression has been assayed in liver, lung and spleen. Luciferase activity was determined by bioluminescence measurement (2–3 mice/point). More than 100 mice have been studied. PCR analysis showed the long lasting expression of the lucriferase gene in all tissues tested (lung, liver, heart, spleen, skeletal muscle, blood cells, bone marrow, and ovary) up to at least 2 months post-injection. Only episomal replicating DNA vectors showed positive results.

EXAMPLE 15

Figure 15:
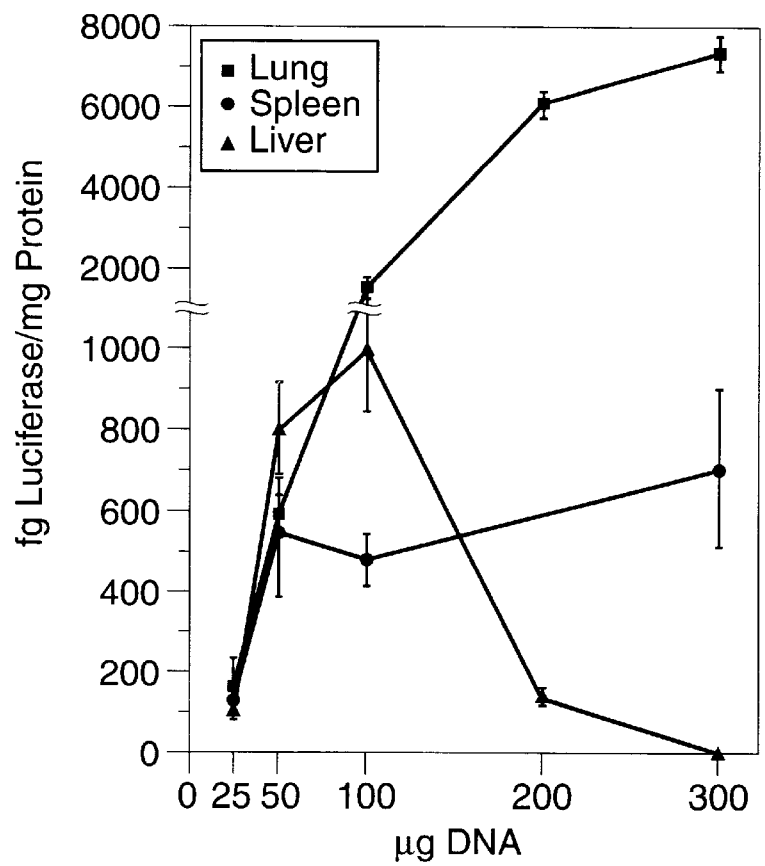
FIG. 15: Dose-response of luciferase DNA expression in different mouse tissues. Increasing amounts of pBKd1RSV-luc plasmid DNA were injected in the mouse tail vein and luciferase activity was determined 4 days post-injection in lung (■), spleen (●) and liver (▲). All determinations of luciferase activity were in triplicate and values are the means (±S.D.) from three different mice.

Intravenous administration of DLS-liposomes containing plasmid DNA: Dose Response Study DNA Dose-Response. To assess for treatment-related toxicity and to determine the optimal liposomal DNA amount to be injected, dose-response experiments were carried out. Episomally replicative pBKd1RSV-luc plasmid DNA encapsulated in DLS liposomes was administered i.v. into mice. Luciferase activity was determined 4 days post-injection in liver, lung, and spleen (FIG. 15). Luciferase activity could be detected in these tissues even when the amount of injected DNA amount was as low as 25 µg/mouse. No significant difference in luc gene expression between tissues was observed at this concentration while at 100 µg DNA injected/mouse a significant difference in activity was observed between lung, liver and spleen (1700±100, 1020±300 and 490±130 fg luciferase/mg protein, respectively; mean ±S.D.). In contrast to lung and spleen where the transgene expression reached a plateau at approximately 200 µg and 50 µg DNA, respectively, there was a decrease in transgene expression in the liver with DNA deliveries greater than 100 µg, perhaps due to toxicity of the liposomal DNA in liver cells or a greater accumulation of liposomal DNA in this organ. No luciferase activity could be detected in liver or lung tissue of mice injected with 100 µg "naked" pBKd1RSV-luc plasmid or the pBKd1RSV plasmid construct containing the lacz gene instead of luc presented in DLS liposomes. Macroscopically slight toxicity was observed (enlarged spleen and pale liver) when 100–500 µg of liposomal DNA were injected into mice. Marked toxicity (grayish lung, tissue damage in heart and occasional death) was observed when more than 150 µg liposomal DNA were administered. No gross or microscopic anatomical pathology was observed at liposomal DNA doses <100 µg. The DNA/lipid ratio was critical as an increase in positively charged lipids may contribute to serious toxicity. The efficiency of DLS liposomes to deliver the transgene depended directly upon the cationic lipid amount in the preparation. Transgene expression in lung greatly increased from 55±20 to 3750±950 fg luciferase/mg protein (mean ±S.D.) when the DNA/lipid ration (w/w) decreased from 0.32 to 0.08. A ratio of 0.08 was optimal and was used throughout this work.

EXAMPLE 16

Figure 16A:
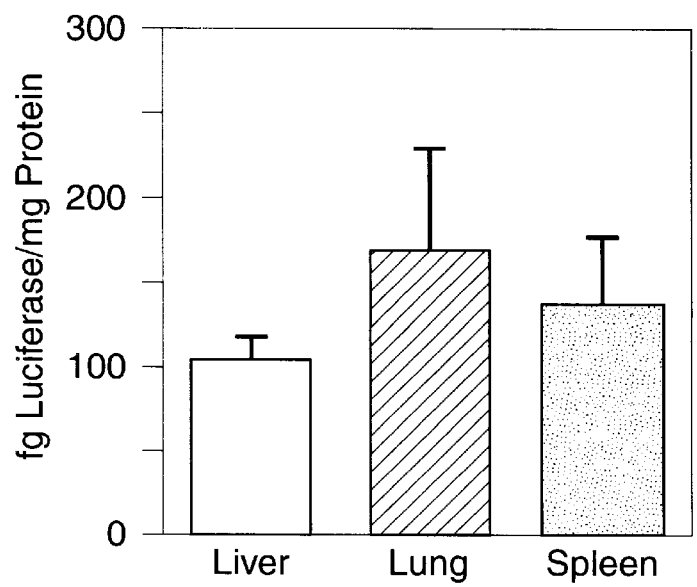
FIGS. 16A–16C: Effect of the route of administration on transgene expression. 25 μg pBKd1RSV-luc plasmid DNA were injected i.v., i.p. and s.c. Luciferase activity was assayed in liver, lung and spleen from two mice sacrificed 4 days after injection. Results are the means (±S.D.) of triplicate luciferase activity determination from two different mice.
Figure 16B:
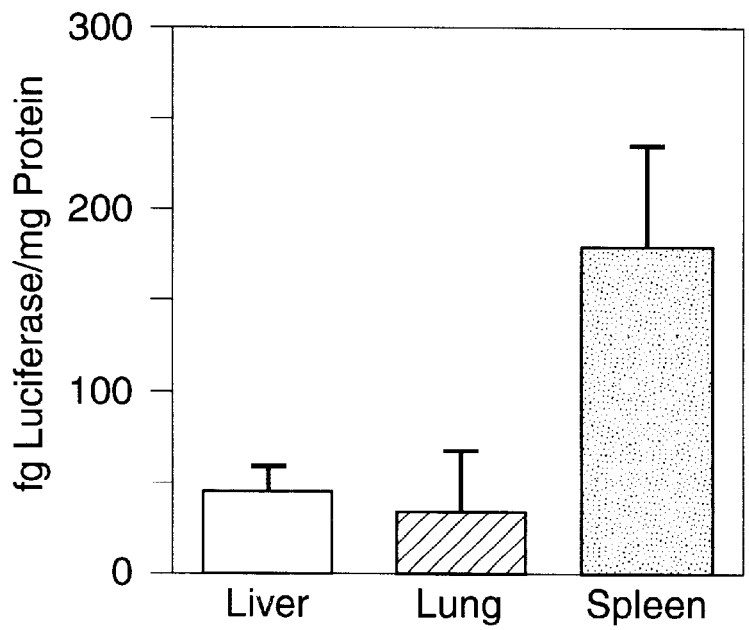
Figure 16C:
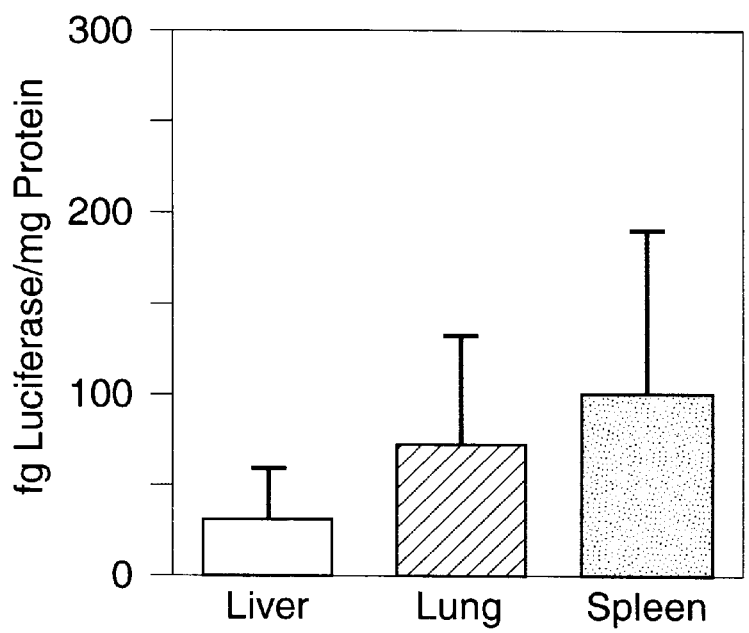

Effect of the Route of Administration. pBKd1RSV-luc plasmid DNA (25 µg) were injected intravenously (i.v.) (tail vein), Intraperitoneally (i.p.) and subcutaneously (s.c.) and luciferase activity was measured 4 days post-injection. No significant difference was observed in the spleen by use of different routes of administration but slightly more activity was detected in the liver and lung with the i.v. route (FIG. 16). S.c. injection appeared to be the less efficient route of administration. I.p. administration resulted in a preferential targeting to the spleen.

Figure 17A:
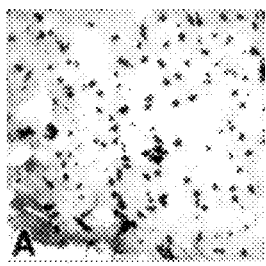
FIGS. 17A–17F: Immunohistochemical detection of luciferase in mice. Animals were treated with 75 μg pBKd2CMV-luc plasmid DNA delivered i.v. with DLS-liposomes-2 liposomes and sacrificed 6 days later. Immunostaining was performed using a horseradish peroxidase-coupled anti-rabbit antibody. Representative immunohistochemical stains on Balb/C mice liver tissue are presented: (A) heart; (B) liver; (D) colon; and (E) Kaposi's sarcoma cells implanted in immunodeficient mice. The sections shown in (C) and (F) are respectively the sections shown in B and E treated with normal rabbit serum in place of anti-luciferase antibody.
Figure 17B:
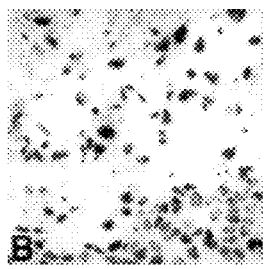
Figure 17C:
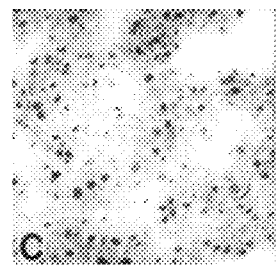
Figure 17D:
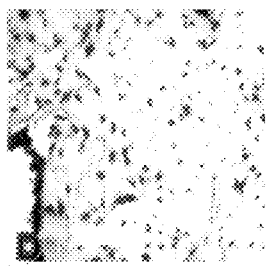
Figure 17E:
Figure 17F:
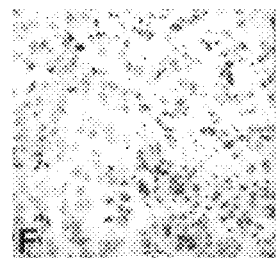

Immunohistochemical Detection of Luciferase Expression. Luciferase expression was detected in tissue samples from mice treated with 75 µg pBKd2CMV-luc and sacrificed 6 days post-injection by immunohistochemical staining using a polyclonal antibody against luciferase protein (FIG. 17). The recombinant protein was detected in all tissues tested although the percentage of positive cells varied: heart, >75%; spleen and liver, >50%; and colon and lung >10%. The pattern of transgene expression was generalized throughout the heart (FIG. 17A, vascular endothelial cells and myocytes), the liver (FIG. 17B, hepatocytes, Kupfer cells and endothelial cells) and the spleen. Although staining intensity was lower in the colon (FIG. 17D) and in lung, staining was also diffuse in these tissues. In separate experiments, 50 pg pBKd1RSV-luc in DLS liposomes were injected i.v. in immunodeficient mice bearing Kaposi's sarcoma (KS Y-1) tumor cells (Lunardi-Iskandar, Y. et al. (1995) Nature 375, 64–68). The luciferase protein was detected in tumor by immunostaining with more than 10% of the tumor cells being positive (FIG. 17E). No positive cells were found in liver (FIG. 17C) or KS Y-1 tumor cells (FIG. 17F) when luciferase antibody was replaced by normal rabbit serum as a control.

EXAMPLE 17

Figure 18A:
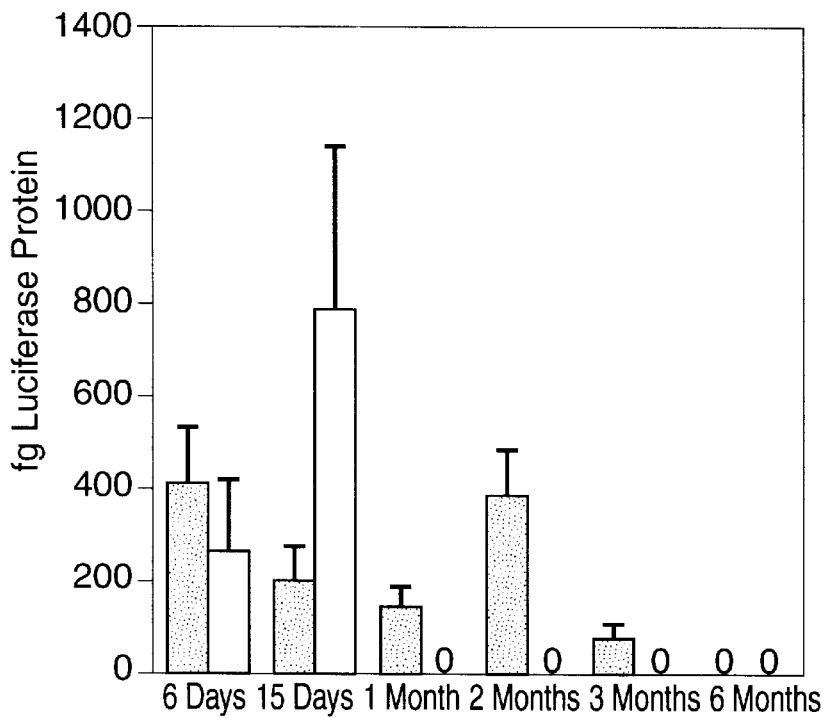
Figure 18B:
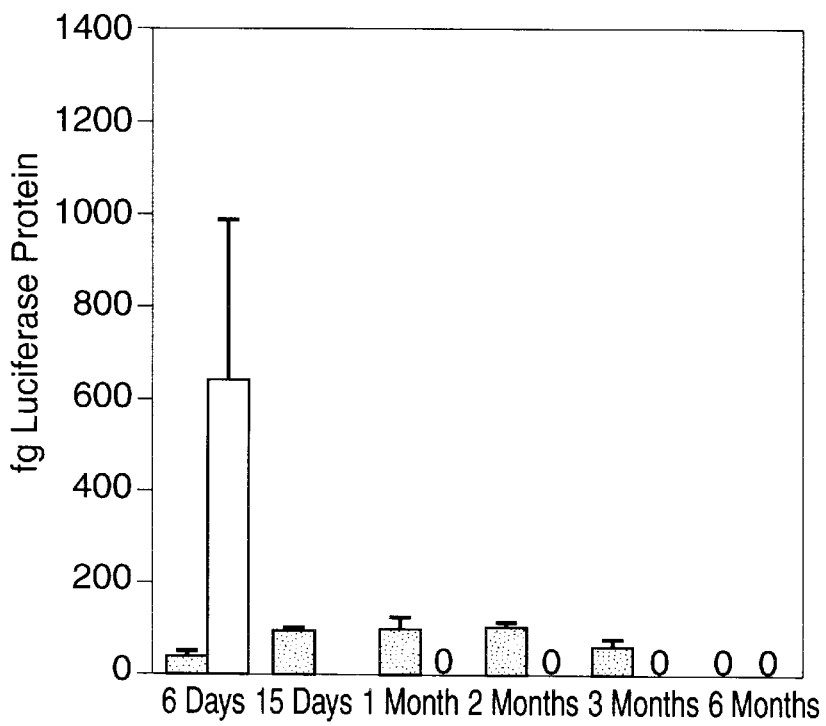

Stability of Luciferase Expression in Different Tissues. pBKd2CMV-luc plasmid DNA (75 μg) was administered i.v. and luciferase activity was measured in liver, lung, spleen and heart at different times (FIG. 18).

TABLE 3

Detection of the luciferase gene in mouse tissues by PCR analyses

| PCR | Liver | Lung | Spleen | Heart | Muscle | BMC | PB | Brain | Ovary |
|---|---|---|---|---|---|---|---|---|---|
| 6 days | 2/2 | 2/2 | 2/2 | 2/2 | 3/3 | 3/3 | 3/3 | ND | 3/3 |
| 2 weeks | ND | ND | ND | ND | 2/2 | 2/2 | ND | 2/2 | 2/2 |
| 1 month | 2/2 | 1/2 | 1/2 | 1/2 | 2/2 | 1/2 | 1/2 | 2/2 | 1/2 |
| 2 months | 2/2 | 2/2 | 1/2 | 1/2 | 2/2 | 2/2 | 1/2 | 0/2 | 0/2 |
| 3 months | 1/1 | 1/1 | 1/1 | 1/1 | 0/1 | 0/1 | 0/1 | 0/1 | 0/2 |
| 6 months | 0/2 | 0/2 | 0/2 | 0/2 | 0/2 | 0/2 | 0/2 | 0/2 | ND |

Number of positive tissues/Number of treated mice.
75 μg of DLS-pBKd2CMV were administered i.v. in mice.
BMC, bone marrow cells; PB, peripheral blood; ND, not determined.

Transgene expression was maximal between 6 and 15 days post-injection in lung, spleen and heart and then gradually declined over 3 months. Luciferase activity was low and constant for up to 3 months in the liver. The luciferase activity was also detected at 6 days in other organs such as the skeleton muscle, brain, bone marrow cells (BMC) and peripheral blood (PB) (398±130, 192±103, 2220±73 and 160±46 fg/mg protein, respectively; mean ±S.D.). Peripheral blood mononuclear cells obtained from whole blood after ficoll purification contained 900 fg/mg protein which corresponded to approximately 1000 detected molecules of luciferase/cell.

PCR analysis confirmed the presence of luciferase activity since all tested tissues were positive for luc 6 days post-injection (Table 3). The transgene was found for up to 1 month in brain and ovary, for up to 2 months in muscle, BMC and PB, and for up to 3 months in lung, liver, spleen and heart. In addition, kidney and colon tissues were positive 2 months post-injection.

Figure 19:
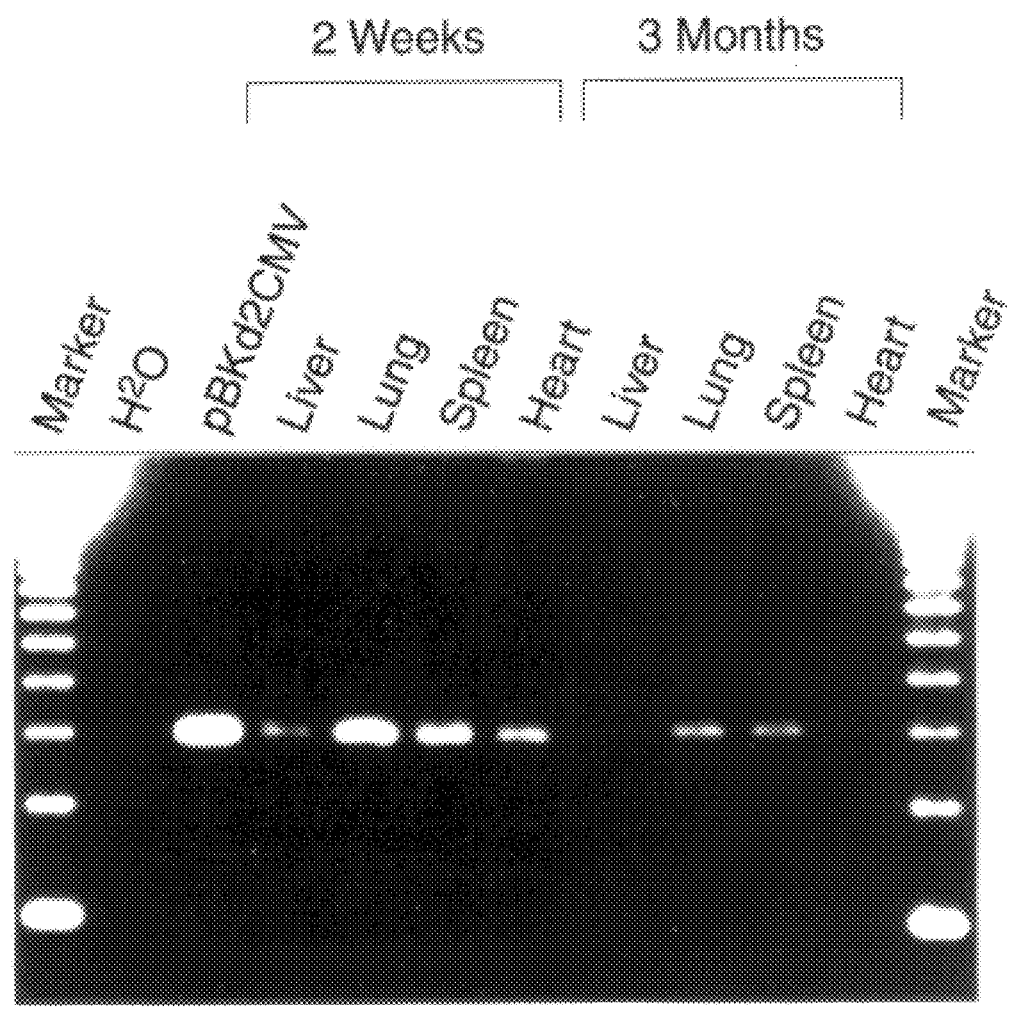
FIG. 19: Luc expression in mouse tissues following i.v. liposomal DNA delivery. Mice were sacrificed 2 weeks and 3 months after administration of 75 μg DLS2-pBKd2CMV-luc. Luciferase mRNA was detected by using a RT-PCR technique on nucleic acids from frozen tissues.
Figure 20A:
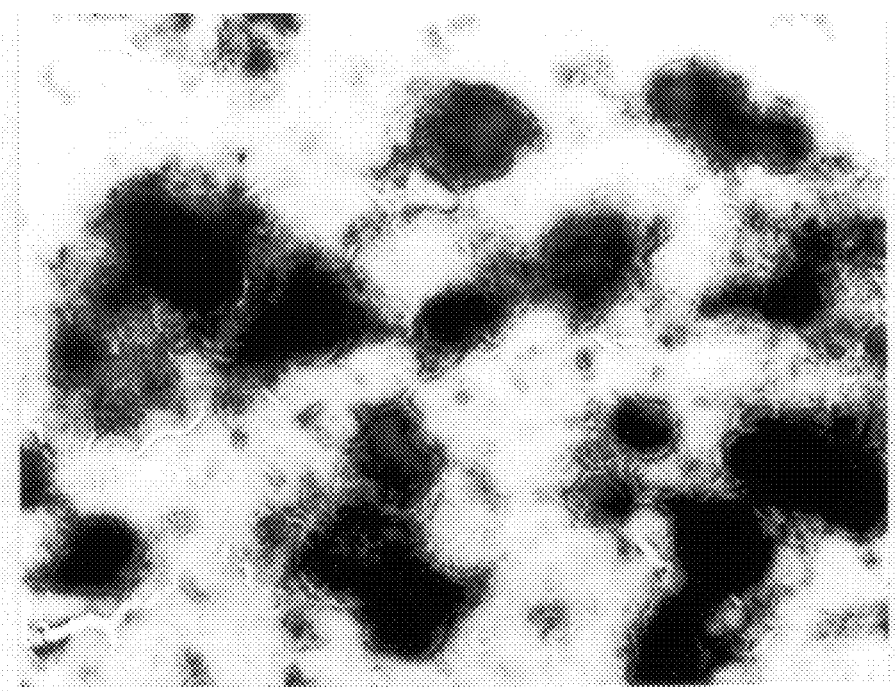
FIGS. 20A–20B: Transmission Election Microseopy comparison. Panel A shows DLS-liposomes and Panel B shows DOGS lipidic particles.
Figure 20B:
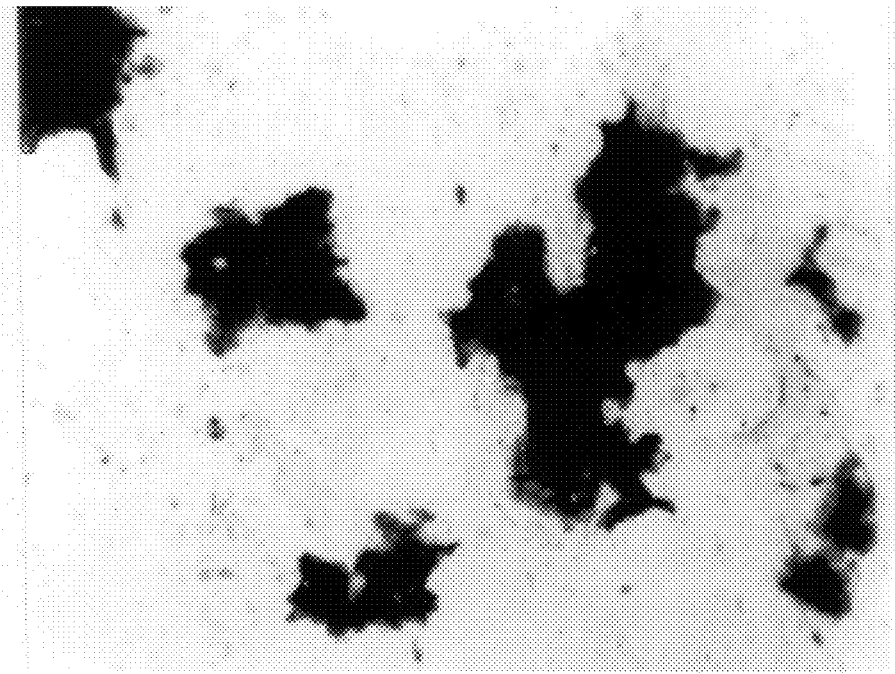

Luc expression was detected by RT-PCR analysis. As shown in FIG. 19, liver, spleen lung were positive 3 months post-injection.

Effect of Plasmid Construct and Promoter on Transgene Expression. The expression of six luciferase plasmids in different organs were compared beginning 6 days after a single i.v. injection of 75 μg DNA delivered with DLS liposomes. The results at 6 days are summarized in Table 4 and show that when using the pRSV-luc plasmid luciferase activity was only detected in lung. In contrast, luciferase activity was high in all tissues tested (liver, lung, spleen and heart) when pCMVintlux was used. The four BKV-derived episomal plasmids showed slightly less or equivalent reporter gene activity. The CMV promoter yielded significantly higher levels of gene expression in spleen and lower levels in lung when compared with the RSV promoter driving the same plasmid DNA construct.

TABLE 4

Plasmid construct and promoter effects on transgene expression

|  | Liver | Lung | Spleen | Heart |
|---|---|---|---|---|
| pRSV-luc | 0 | ++ | 0 | 0 |
| pCMVintlux | ++ | +++ | ++ | +++ |
| pBKd1RSV-luc | + | ++ | ++ | +++ |
| pBKd1CMV-luc | ++ | +* | +++† | +++ |

TABLE 4-continued

Plasmid construct and promoter effects on transgene expression

|  | Liver | Lung | Spleen | Heart |
|---|---|---|---|---|
| pBKd2RSV-luc | ++ | +++ | + | ++ |
| pBKd2CMV-luc | + | ++‡ | +++§ | ++ |

Relative luciferase activity: 0, not detectable; +, 0–0.1 pg/mg protein; ++, 0.1–1.0 pg/mg protein; +++, higher than 1.0 pg/mg protein. i.v. administration, activity determined 6 days post-injection. pBKd1CMV-luc versus pBKd1RSV-luc in *lung (p = 0.011) and in †spleen (p = 0.001), and pBKd2CMV-luc versus pBKd2RSV-luc in $^{555}$lung (p = 0.187) and in $^{517}$spleen (p = 0.021).

The time course of luc expression in mouse tissues from the non-replicative pCMVintlux and episomal pBKd2CMV-luc plasmid constructs was followed after a single i.v. injection of 75 Ag DNA (FIG. 17). Luc product expressed from pBKd2CMV-luc was detected in lung, liver, spleen and heart for up to 2–3 months post-injection. No detection of luciferase activity was observed in these tissues 1 month after injection of pCMVintlux.

EXAMPLE 18

Intraperitoneal administration of DLS-liposomes containing DNA.

Luciferase gene expression was detected in spleen 3 days post-injection. The dose injected per mouse was 100 ug. No toxicity was detected.

EXAMPLE 19

Inhibition of KS Y-1 cell tumorigenicity.

The present invention can be used in the therapy of Kaposi's Sarcoma ("KS"). Two KS cell lines, showing tumorigenic properties in vitro and in vivo, have recently been established. One cell line, KS Y-1, was derived from a lesion of an HIV-infected individual. The second cell line, KS N1506, was derived from a lesion of a non-HIV associated immunodepressed individual. High amounts of IL-6, IL-8, and VEGF are produced in these cell lines. Correspondingly, high levels of these cytokines have also been found in the serum of AIDS-KS patients. In this example, antisense oligo(dN) was used as a specific molecular tool to inhibit KS cell production of these factors.

0.1 uM VEGF antisense phosphodiester oligodeoxynucleotides encapsulated in DLS-liposomes completely blocked KS Y-1 cell colony formation in semi-solid culture. Lipofectin™ liposomes required 7–10 fold higher concentration to achieve the same inhibitory effect.

What is claimed is:

1. A composition comprising a bi- or multi-layer membrane surrounding an internal aqueous liposome comprising at least one cationic lipopolyamine and at least one neutral lipid provided in a molar ratio range said ratio from about 0.02:1 to about 2.0:1.

2. A composition according to claim 1 wherein the lipopolyamine comprises a quaternary or tertiary polyamine lipid.

3. A composition according to claim 2 wherein at least one cationic lipopolyamine is selected from the group consisting of 2,3-dioleyloxy-N[2 (sperminecarboxamido)ethyl]-N,N-dimethyl-1-propanaminium trifluoracetate, N[1-(2,3-dioleyloxy) propyl]-N,N,N-trimethyl-ammonium chloride and Spermine-5-carboxy-glycinediotadecylamide.

4. A composition according to claim 3 wherein the cationic lipopolyamine comprises at least one spermine-5-carboxy-glycinedioctadecylamide.

5. A composition according to claim 1 wherein the neutral lipid is a neutral amino phospholipid.

6. A composition according to claim 5 wherein the neutral lipid is selected from the group consisting of dioleylphosphatidyl ethanolamine and phosphatidylethanolamine.

7. A composition of claim 1 wherein the cationic lipopolyamine comprises spermine-5-carboxy-glycinediocadecylamide and the neutral lipid comprises dioleylphosphatidyl ethanolamine.

8. A composition of claim 1 wherein the cationic lipopolyamine comprises spermine-5-carboxy-glycindioctadecylamide and the neutral lipid comprises phosphatidylethanolamine.

9. A composition according to claim 1 or 7 further comprising a biologically active agent.

10. A composition according to claim 9 wherein the biologically active agent is selected from the group consisting of a therapeutic agent, a protein or a nucleic acid.

11. A composition according to claim 10 wherein the nucleic acid is selected from the group consisting of a chromosome of a chromosomal fragment, a deoxyribonucleic acid, a ribonucleic acid, a ribozyme, an oligonucleotide, an anti-sense oligonucleotide, a plasmid DNA or a nucleic acid viral in origin.

12. A method of preparing a liposome comprising the steps of:

(a) mixing a cationic lipopolyamine with a neutral lipid in a molar ratio range of about 0.02:1 to about 2.0:1, forming a mixture;

(b) evaporating the mixture to dryness, forming a dried film;

(c) adding a biologically active agent;

(d) rehydrating the dried film with said biologically active agent forming the liposome.

13. The method of claim 12 wherein the biologically active agent is a nucleic acid solution provided in a ratio of 40–240 microgram nucleic acid per milligram lipid.

14. The method of claim 13 wherein said nucleic acid is provided in a concentration of about 1–3 mg/ml.

15. The method of claim 13 further comprising rehydrating the dried film in a solution having a pH of 5.5–6.5.

16. The method of claim 13 wherein the aqueous solution is water.

17. A method of introducing a biologically active agent into cells of a subject comprising administrating to the subject an effective amount of a composition according to claim 9.

18. The method of claim 17 wherein the biologically active agent is a nucleic acid.

19. The method of claim 18 wherein the nucleic acid is a DNA.

20. A composition of claim 9 wherein the biologically active agent comprises adenovirus particles.

21. A composition according to claim 9 further comprising adenovirus particles.

* * * * *